US012239292B2

(12) United States Patent
Ibrahim et al.

(10) Patent No.: US 12,239,292 B2
(45) Date of Patent: Mar. 4, 2025

(54) CLIP APPLICATION SYSTEM AND METHOD

(71) Applicant: AtriCure, Inc., Mason, OH (US)

(72) Inventors: Tamer Ibrahim, Danville, CA (US);
Dwight P. Morejohn, Davis, CA (US);
Matthew Monti, Cincinnati, OH (US);
Kenneth L. Miller, Hamilton, OH (US); Michael J. Banchieri, Discovery Bay, CA (US); Brian Flores, Castro Valley, CA (US); Ara Stephanian, Davis, CA (US); Kimberly Cunningham, Florence, KY (US);
Robert M. Trusty, Cincinnati, OH (US); Stefan Stefanov, Ludlow, KY (US); Anthony Sticca, Mason, OH (US)

(73) Assignee: AtriCure, Inc., Mason, OH (US)

( * ) Notice: Subject to any disclaimer, the term of this patent is extended or adjusted under 35 U.S.C. 154(b) by 534 days.

(21) Appl. No.: 16/740,084

(22) Filed: Jan. 10, 2020

(65) Prior Publication Data

US 2020/0222055 A1    Jul. 16, 2020

Related U.S. Application Data

(60) Provisional application No. 62/790,633, filed on Jan. 10, 2019.

(51) Int. Cl.
*A61B 17/128*    (2006.01)
*A61B 1/00*    (2006.01)
(Continued)

(52) U.S. Cl.
CPC .......... *A61B 1/018* (2013.01); *A61B 1/00066* (2013.01); *A61B 1/005* (2013.01);
(Continued)

(58) Field of Classification Search
CPC .............. A61B 17/128; A61B 17/1285; A61B 2017/00234; A61B 2017/00243; A61B 2017/0034; A61B 2017/00473; A61B 2017/00946; A61B 1/00066; A61B 1/005; A61B 1/018; A61B 17/3423; A61B 17/3462; A61B 2017/3429; A61B 17/068
See application file for complete search history.

(56) References Cited

U.S. PATENT DOCUMENTS 5,626,607 A * 5/1997 Malecki ........... A61B 17/00234
606/205
5,667,480 A * 9/1997 Knight ............. A61B 17/00234
606/190

(Continued)

*Primary Examiner* — Diane D Yabut
*Assistant Examiner* — Christian D Knauss
(74) *Attorney, Agent, or Firm* — Dorton & Willis LLP; Ryan Willis

(57) ABSTRACT

An example system for applying an occlusion clip to an anatomical structure may include a visualization tool configured to allow visualization of an anatomical structure using a scope; a clip applier configured to apply an occlusion clip on the anatomical structure; an introducer connectable to the clip applier and configured to aid in positioning the clip applier; and a positioner configured to apply at least one of a linear force and a torsional force to at least one of the clip applier and the clip.

14 Claims, 19 Drawing Sheets

(51) Int. Cl.
 *A61B 1/005* (2006.01)
 *A61B 1/018* (2006.01)
 *A61B 17/00* (2006.01)
 *A61M 25/06* (2006.01)
 *A61M 25/09* (2006.01)

(52) U.S. Cl.
 CPC .. *A61B 17/1285* (2013.01); *A61B 2017/0034* (2013.01); *A61B 2017/00473* (2013.01); *A61B 2017/00946* (2013.01); *A61M 2025/0681* (2013.01); *A61M 25/09* (2013.01)

(56) References Cited

U.S. PATENT DOCUMENTS

| | | | |
|---|---|---|---|
| 6,770,081 B1* | 8/2004 | Cooper | A61B 34/71 606/130 |
| 8,636,754 B2 | 1/2014 | Hughett, Sr. et al. | |
| 9,017,349 B2 | 4/2015 | Privitera et al. | |
| 9,861,371 B2 | 1/2018 | Martin et al. | |
| 9,883,867 B2 | 2/2018 | Martin et al. | |
| 9,901,351 B2 | 2/2018 | Winkler et al. | |
| 9,901,352 B2 | 2/2018 | Fago et al. | |
| 10,201,352 B2 | 2/2019 | Fago et al. | |
| 2001/0049540 A1* | 12/2001 | Santilli | A61B 17/128 606/158 |
| 2004/0204725 A1* | 10/2004 | Bayer | A61B 18/1482 606/159 |
| 2006/0217666 A1* | 9/2006 | Wenchell | A61B 17/3417 604/167.03 |
| 2010/0331862 A1* | 12/2010 | Monassevitch | A61B 17/1285 606/151 |
| 2015/0083776 A1* | 3/2015 | Lim | A61B 17/07207 29/401.1 |
| 2016/0106300 A1* | 4/2016 | Noyes | A61B 1/00135 600/106 |
| 2019/0142428 A1 | 5/2019 | Widenhouse et al. | |

* cited by examiner

CLIP APPLICATION SYSTEM AND METHOD

CROSS REFERENCE TO RELATED APPLICATIONS

This application claims the benefit of U.S. Provisional Application No. 62/790,633, filed Jan. 10, 2019, which is incorporated by reference.

INTRODUCTION TO THE INVENTION

The present disclosure is directed to medical instruments and devices and related methods, and, more specifically, to systems for applying occlusion devices on anatomical structures, such as an occlusion clip on a left atrial appendage of a heart, and related methods.

The present disclosure contemplates that atrial fibrillation is a common heart arrhythmia, affecting millions of people in the United States. The present disclosure contemplates that, in some circumstances, it may be desirable to occlude an anatomical structure by placing an occlusion device, such as an occlusion clip, on the anatomical structure. For example, in some patients with atrial fibrillation, stagnant blood in the heart's left atrial appendage ("LAA") may be a source of blood clots, which may enter the blood circulation and increase the risk of stroke. Excluding the LAA, which may create electrical and/or fluidic isolation of the LAA, may be beneficial in terms of reducing the atrial fibrillation burden and/or reducing the risk of stroke for some patients. Accordingly, in some patients, it may be desirable to exclude the LAA by securely sealing the LAA orifice at the base of the LAA using an occlusion clip. U.S. Pat. Nos. 8,636,754; 9,017,349; 9,861,371; 9,883,867; 9,901,351; 9,901,352; and 10,201,352; and U.S. Patent Application Publication No. 2019/0142428, relate to LAA occlusion devices and methods and are incorporated by reference herein.

It is an aspect of the present disclosure to provide a system for applying an occlusion clip to an anatomical structure including a visualization tool configured to allow visualization of an anatomical structure using a scope; a clip applier configured to apply an occlusion clip on the anatomical structure; and/or an introducer connectable to the clip applier and configured to aid in positioning the clip applier proximate the anatomical structure.

In a detailed embodiment, the system may include a positioner configured to apply at least one of a linear force and a torsional force to at least one of the clip applier and the occlusion clip. The visualization tool may include an elongated, generally rigid shaft; a handle disposed at a proximal end portion of the shaft; and/or a scope hood disposed at a distal end portion of the shaft. The visualization tool may include a first channel extending longitudinally through the shaft. The first channel may be configured to receive at least one of a guidewire, a guide sheath, and the introducer therethrough. The scope may include an endoscope. The endoscope may extend through a second channel extending longitudinally through the shaft.

In a detailed embodiment, the visualization tool may include an elongated, substantially malleable shaft; a handle disposed at a proximal end portion of the shaft; and/or a scope hood disposed at a distal end portion of the shaft.

In a detailed embodiment, the introducer may include an elongated, generally flexible distal section and an elongated, generally flexible proximal section. A proximal end portion of the distal section may be configured to releasably couple to a distal end portion of the proximal section. The proximal end portion of the distal section may include a first connector and the distal end portion of the proximal section may include a second connector. The first connector and the second connector may be releasably connectable. The clip applier may include a distal tip portion. The distal tip portion may include a third connector. The second connector may be connectable to the third connector to connect the introducer to the clip applier. When the second connector is connected to the third connector, the second connector and the third connector may not be readily detachable by pulling apart the second connector and the third connector. The clip applier may include a first jaw and a second jaw. At least one of the first jaw and the second jaw may be articulable to open and close the occlusion clip. The first jaw may include a jaw member and the distal tip portion. The distal tip portion may be releasably attached to the jaw member.

It is an aspect of the present disclosure to provide an occlusion clip applier including an elongated shaft; a handle disposed at a proximal end portion of the shaft; and/or an end effector disposed at a distal end portion of the shaft. The end effector may be configured to deliver and apply an occlusion clip onto an anatomical structure. The end effector may include a distal tip portion that is connectable to the distal end portion of an elongated, flexible introducer.

In detailed embodiment, the shaft may be at least one of substantially rigid, generally flexible, substantially malleable, and steerable. The shaft may be capable of transmitting torque between the handle and the end effector.

In a detailed embodiment, the end effector may include at least one articulation joint. The shaft may be substantially malleable.

In a detailed embodiment, the shaft may include a generally flexible inner shaft and a generally malleable outer shaft. The outer shaft may be substantially shorter than the inner shaft. The outer shaft may be axially slidably disposed on the inner shaft.

In a detailed embodiment, the end effector may include a first jaw and a second jaw. At least one of the first jaw and the second jaw may be articulable to open and close the occlusion clip. The first jaw may include a jaw member and the distal tip portion. The distal tip portion may be releasably attached to the jaw member. The occlusion clip may include an open-ended occlusion clip releasably coupled to the first jaw and the second jaw. A distal portion of the second jaw may be generally rounded to facilitate atraumatic insertion and positioning of the end effector.

In a detailed embodiment, the distal end portion of the introducer may include a first connector. The distal tip portion of the end effector may include a second connector. The first connector and the second connector may be connectable. The first connector may be configured to releasably couple with the second connector. The first connector and the second connector may be configured so that, when connected together, the first connector and the second connector are not readily detachable by pulling apart the first connector and the second connector.

In a detailed embodiment, one of the first connector and the second connector may include a latch. The other of the first connector and the second connector may include a flange. When the first connector and the second connector are connected, the latch may engage the flange to prevent the first connector and the second connector from separating. The latch may be disposed on an elastically deformable arm.

In a detailed embodiment, one of the first connector and the second connector may include a radially extending projection. The other of the first connector and the second connector may include a slot. When the first connector and the second connector are connected, the projection may be retained in the slot. The slot may include a generally longitudinal entry slot, a generally circumferential rotation slot, and/or a generally longitudinal, dead-end locking slot. When the first connector and the second connector are connected, the projection may be retained in the locking slot.

In a detailed embodiment, one of the first connector and the second connector may include a longitudinally extending spring arm. The other of the first connector and the second connector may include a generally axially facing surface arranged to engage the spring arm. When the first connector and the second connector are connected, the axially facing surface may elastically deform the spring arm. The elastically deformed spring arm may exert a separating force on the first connector and the second connector. The separating force may retain the projection in the locking slot.

It is an aspect of the present disclosure to provide an introducer for an occlusion clip applier including an elongated, generally flexible distal section and/or an elongated, generally flexible proximal section. A proximal end portion of the distal section may be releasably couplable to a distal end portion of the proximal section. The distal end portion of the proximal section may be couplable to a distal tip portion of a clip applier configured to apply an occlusion clip to an anatomical structure.

In a detailed embodiment, the proximal end portion of the distal section may include a first connector. The distal end portion of the proximal section may include a second connector. The distal tip portion of the clip applier may include a third connector. The first connector may be releasably couplable to the second connector. The second connector may be couplable to the third connector. A proximal end portion of the proximal section may include a fourth connector. The second connector and the fourth connector may be substantially the same. The second connector may be releasably couplable to the third connector. The second connector and the third connector may be configured so that, when connected together, the second connector and the third connector may not be readily detachable by pulling apart the second connector and the third connector. The distal tip portion may be releasably connected to a jaw member of an end effector of the clip applier.

In a detailed embodiment, a distal end portion of the distal section may be tapered to provide a generally conical tip. The proximal section may have a generally constant outer diameter.

It is an aspect of the present disclosure to provide a method of excluding a left atrial appendage including advancing a visualization tool through an incision and to a position proximate a right, anterior portion of a heart; advancing an elongated, flexible introducer anterior to a superior vena cava and posterior to an aorta into a transverse sinus; advancing a distal end portion of the introducer through the transverse sinus and out of the transverse sinus on a left side of the heart proximate a left atrial appendage; connecting the distal end portion of the introducer to a distal tip portion of a clip applier; advancing the clip applier to the left atrial appendage by pushing on the clip applier and pulling on the introducer; and/or deploying an occlusion clip from the clip applier onto the left atrial appendage.

In a detailed embodiment, the introducer may include a releasably coupled proximal section and distal section. Advancing the distal end portion of the introducer through the transverse sinus may include advancing the distal section and a distal end portion of the proximal section through the transverse sinus. Connecting the distal end portion of the introducer to the distal tip portion of the clip applier may include connecting the distal end portion of the proximal section to the distal tip portion. A proximal end portion of the distal section may include a first connector, the distal end portion of the proximal section may include a second connector, and/or the distal tip portion may include a third connector. Connecting the distal end portion of the proximal section to the distal tip portion may include disconnecting the first connector from the second connector and connecting the second connector to the third connector. One of the first connector and the second connector may include a latch and the other of the first connector and the second connector may include a flange arranged to engage the latch. Disconnecting the first connector from the second connector may include disengaging the latch from the flange. One of the first connector and the second connector may include a locking slot and the other of the first connector and the second connector may include a projection configured to engage the locking slot. Disconnecting the first connector from the second connector may include disengaging the projection from the locking slot.

In a detailed embodiment, the distal tip portion may be releasably disposed on a jaw member of the clip applier. The method may include releasing the distal tip portion from the jaw member. Releasing the distal tip portion from the jaw member may include operating an actuator on a handle of the clip applier. Releasing the distal tip portion from the jaw member may include keeping the distal end portion of the introducer connected to the distal tip portion of the clip applier.

In a detailed embodiment, advancing the introducer into the transverse sinus may include advancing a guidewire into the transverse sinus and advancing the introducer along the guidewire. Advancing the introducer into the transverse sinus may include advancing the introducer through a working channel in the visualization tool. Advancing the clip applier to the left atrial appendage may include applying at least one of a linear force and a torsional force to the clip applier using a positioner extending through the incision. The method may include, before advancing the visualization tool through the incision, making the incision, the incision being at least one of a sub-xiphoid and a sub-costal incision.

It is an aspect of the present disclosure to provide a method of excluding a left atrial appendage including advancing a visualization tool through at least one of a sub-xiphoid incision and a sub-costal incision and to proximate a left, anterior portion of a heart; bending a malleable shaft of a clip applier; advancing the clip applier to a left atrial appendage of the heart; and/or deploying an occlusion clip from the clip applier onto the left atrial appendage.

In a detailed embodiment, the clip applier may include an end effector disposed at a distal end portion of the shaft, the occlusion clip being releasably attached to the end effector. The method may include, before deploying the occlusion clip, articulating the end effector with respect to the shaft.

In a detailed embodiment, the method may include, before deploying the occlusion clip, applying at least one of a linear force and a torsional force to the clip applier using a positioner extending through the at least one of the sub-xiphoid incision and the sub-costal incision. The method may include, before deploying the occlusion clip, positioning the occlusion clip on the left atrial appendage and/or verifying a position of the occlusion clip on the left atrial appendage using an imaging technique.

BRIEF DESCRIPTION OF THE DRAWINGS

Example embodiments are described in conjunction with the accompanying drawing figures in which.

DETAILED DESCRIPTION

Example embodiments according to the present disclosure are described and illustrated below to encompass devices, methods, and techniques relating to medical procedures. Of course, it will be apparent to those of ordinary skill in the art that the embodiments discussed below are examples and may be reconfigured without departing from the scope and spirit of the present disclosure. It is also to be understood that variations of the example embodiments contemplated by one of ordinary skill in the art shall concurrently comprise part of the instant disclosure. However, for clarity and precision, the example embodiments as discussed below may include optional steps, methods, and features that one of ordinary skill should recognize as not being a requisite to fall within the scope of the present disclosure.

The present disclosure includes, inter alia, medical instruments and devices and related methods, and, more specifically, systems for applying occlusion devices and related methods. Some example embodiments according to at least some aspects of the present disclosure may be particularly useful in connection with cardiac procedures, such as to treat cardiac arrhythmias like atrial fibrillation, for the reasons discussed above in the Introduction section and the patent references incorporated by reference herein.

The present disclosure contemplates that some known procedures for placing a LAA occlusion device may involve various surgical access methods, including sternotomy, thoracotomy, and/or port access through the ribcage. The present disclosure contemplates that some patients may benefit from a LAA exclusion procedure that may be performed using a sub-xiphoid or sub-costal approach.

Figure 1:
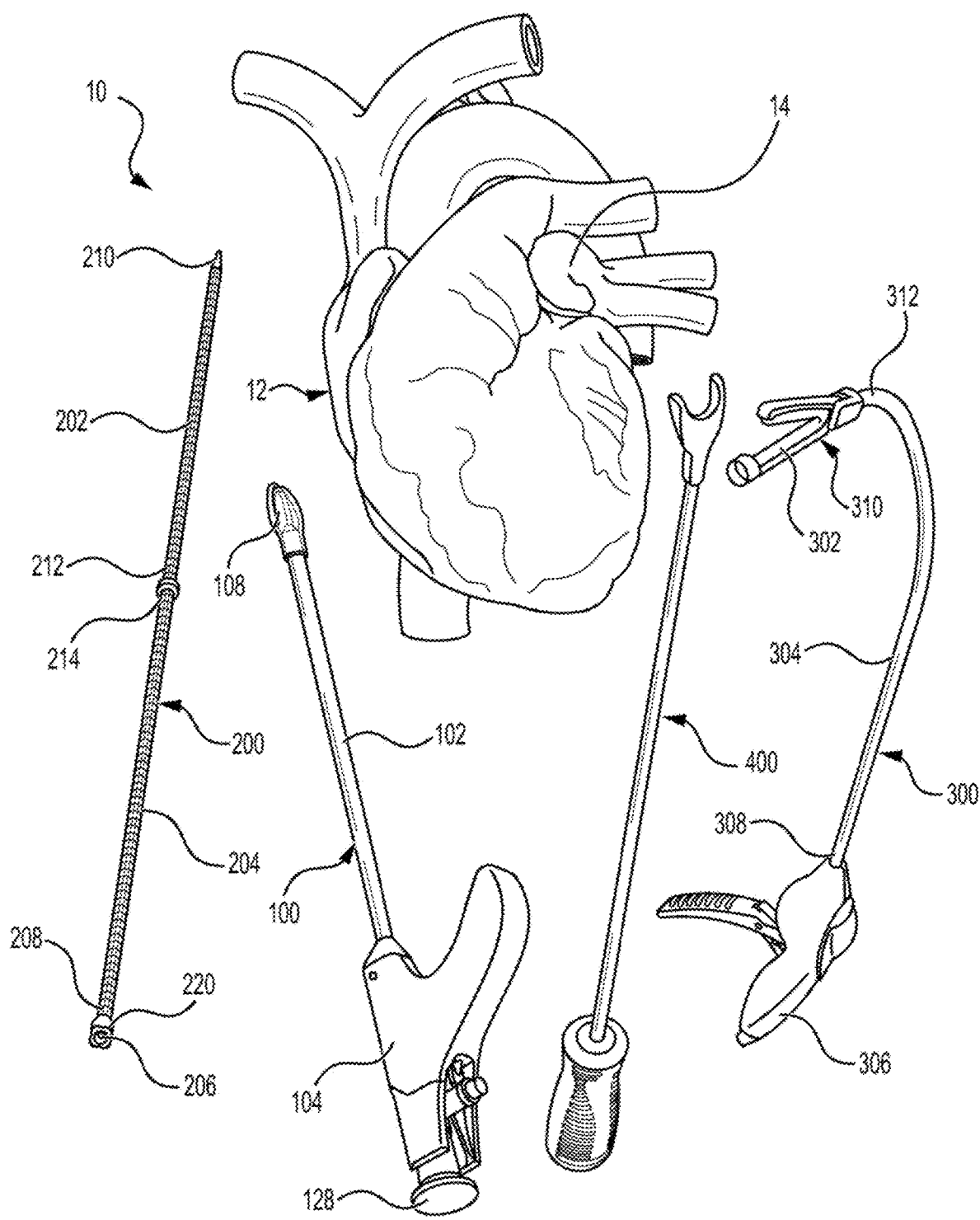
FIG. 1 is a schematic view of an example clip application system and a heart.

FIG. 1 is a schematic view of an example clip application system 10 and a heart 12, according to at least some aspects of the present disclosure. The clip application system 10 may include a visualization tool 100, an introducer 200, a clip applier 300, and/or a positioner 400. Generally, the clip application system 10 may be used in connection with applying an occlusion clip 302 onto the left atrial appendage 14 of the heart 12. As used herein, "occlusion clip" may refer broadly to any occlusion device that is applied to an occludable anatomical structure in a generally similar manner.

Figure 2:
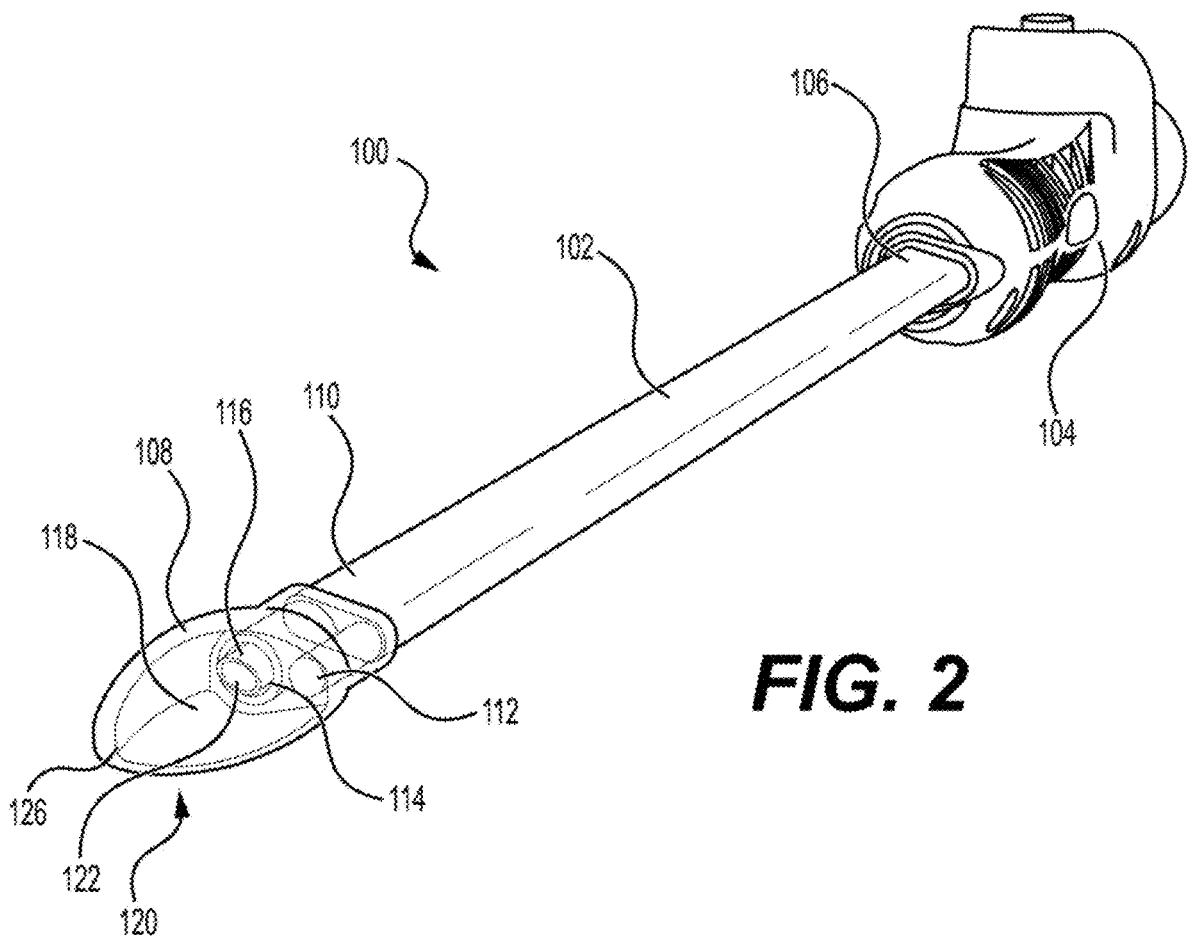
FIG. 2 is a distal isometric view of an example visualization tool.

FIG. 2 is a distal isometric view of an example visualization tool 100, according to at least some aspects of the present disclosure. Referring to FIGS. 1 and 2, the visualization tool 100 may include an elongated shaft 102, a handle 104 disposed at a proximal end portion 106 of the shaft 102, and/or a scope hood 108 disposed at a distal end portion 110 of the shaft 102. As used herein, "distal" may refer generally to the direction towards the portion of a surgical device that is inserted into a patient's body, and "proximal" may refer generally to the direction towards the portion of a surgical device that remains outside of the patient's body.

In some example visualization tools 100, the shaft 102 may include one or more channels 112, 114 extending longitudinally therethrough, such as between the handle 104 and the scope hood 108. In some example embodiments, a first channel 112 may be configured as a working channel, such as to receive other surgical instruments or devices (e.g., a guidewire, a guide sheath, and/or the introducer 200) therethrough. For example, the working channel 112 may be configured to accommodate devices up to about 8 French in diameter. In some example embodiments, the shaft 102 may be generally rigid and/or substantially malleable, which may facilitate positioning and/or visualization, such as by separating pericardial tissues away from the heart.

In some example visualization tools 100, a second channel 114 may be configured to receive a scope 116, such as an endoscope. As used herein, "scope" may refer to an optical device used to observe an area within a patient's body and may include rigid or flexible endoscopes, laparoscopes, arthroscopes, bronchoscopes, ureteroscopes, etc. A scope may include a lighting feature and/or may be utilized with a separate lighting device, either of which may be used to illuminate the field of view of the scope. Further, scopes as described herein may include "chip on the tip" configurations in which a video sensor and/or a light source are permanently embedded into a device, such as proximate the distal end of an instrument. For example, a visualization tool 100 including a "chip on the tip" configuration may include a video sensor disposed to view proximate the scope hood 108 and/or may not include a separate scope channel 114 in addition to the working channel 112.

Figure 3:
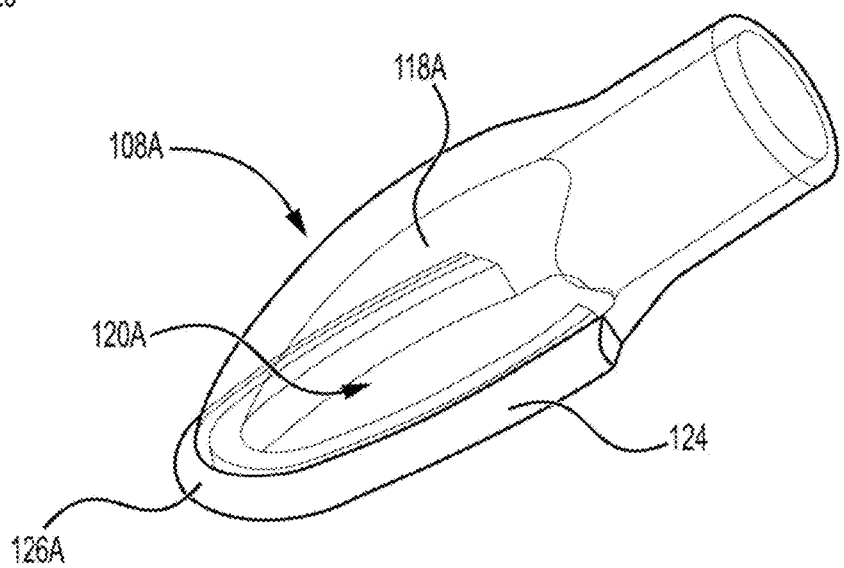
FIG. 3 is a detailed distal isometric view of an alternative example scope hood.

FIG. 3 is a detailed distal isometric view of an alternative example scope hood 108a of the visualization tool 100, according to at least some aspects of the present disclosure. Referring to FIGS. 1-3, in some example embodiments, the scope hood 108, 108a may be generally rounded and/or may include an interior volume 118, 118a that is contiguous with the interior of the working channel 112 and/or the scope channel 114. The interior volume 118, 118a may be contiguous with the exterior of the visualization tool 100 via an opening, such as a lateral opening 120, 120a. Accordingly, a device (e.g., a guidewire and/or the introducer 200) extended through the working channel 112 may extend out of the opening 120, 120a.

In some example visualization tools 100, the scope hood 108, 108a may be configured to maintain a separation between the patient's internal anatomic structures and the distal tip 122 of the scope 116 to facilitate viewing through the scope 116. In some example embodiments, at least a portion of the scope hood 108, 108a may be constructed from a generally transparent material, such as substantially clear plastic. In some such embodiments, the scope 116 may be configured to allow viewing through the scope hood 108, 108a. Some example scope hoods 108, 108a may include an atraumatic edge, such as a polymer rim 124, disposed about the opening 120, 120a and/or at the distal tip portion 126, 126a of the scope hood 108.

Referring to FIG. 1, some example visualization tools 100 may include one or more proximal openings 128 through which devices, such as guidewires, guide sheaths, introducers 200, and/or scopes 116, may be advanced through the channels 112, 114.

Figure 4:
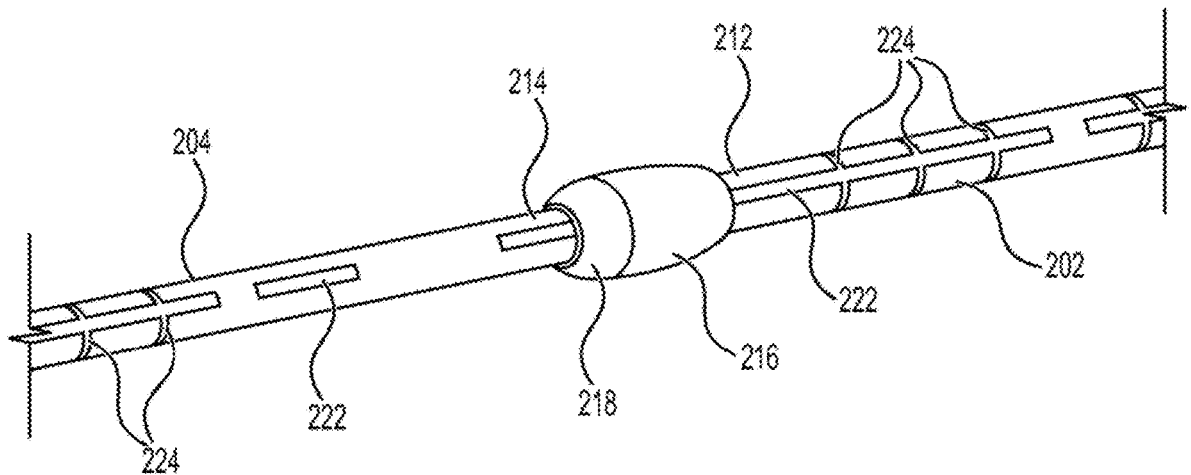
FIG. 4 is a detailed isometric view of a portion of an example introducer.
Figure 5:
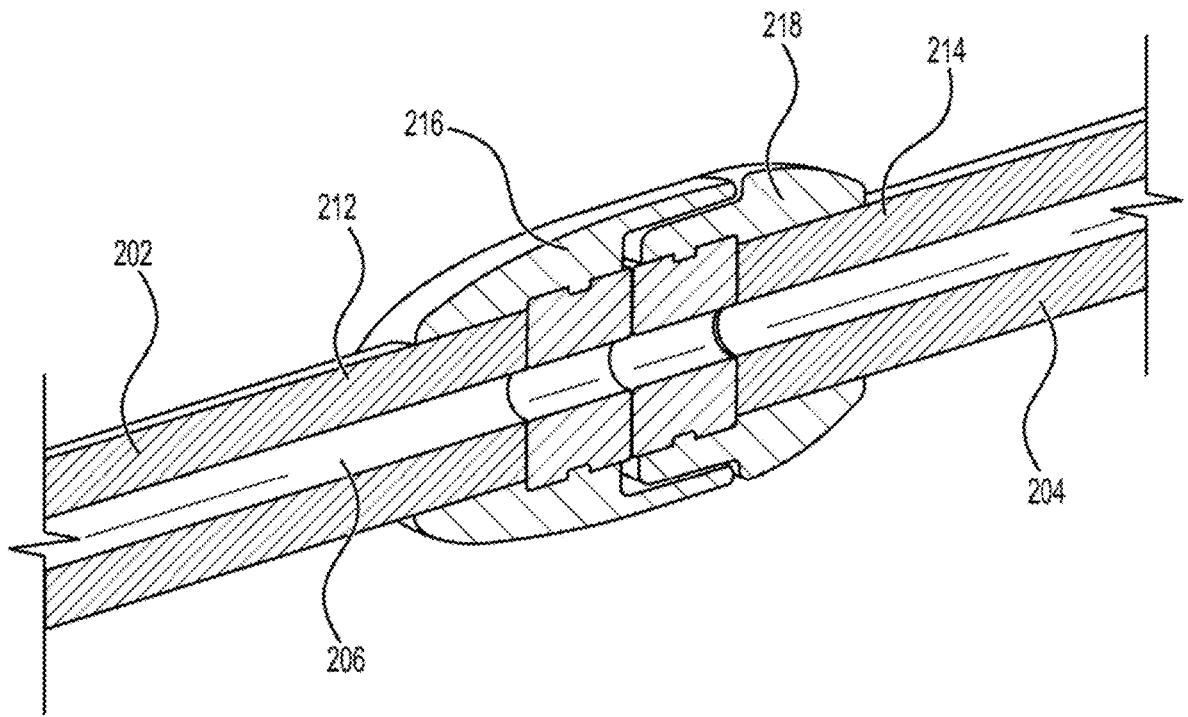
FIG. 5 is a detailed isometric cross-sectional view of a portion of an example introducer.

FIG. 4 is a detailed isometric view of a portion of the introducer 200 and FIG. 5 is a detailed isometric cross-sectional view of a portion of the introducer 200, according to at least some aspects of the present disclosure. Referring to FIGS. 1, 4 and 5, the introducer 200 may include an elongated, generally flexible distal section 202 and/or an elongated, generally flexible proximal section 204. The introducer 200 may be generally tubular, including a longitudinal lumen 206, which may be configured to receive a guidewire therethrough. The lumen 206 may extend from a proximal end portion 208 of the proximal section 204 to a distal end portion 210 of the distal section 202.

In some example introducers 200, the proximal section 204 may have a generally constant outer diameter and/or the distal end portion 210 of the distal section 202 may be generally tapered, such as in a generally conical shape, to provide a generally tapered tip. The tapered tip may facilitate entry into tissue planes.

In some example introducers 200, a proximal end portion 212 of the distal section 202 may be configured to releasably couple to a distal end portion 214 of the proximal section 204, such as by respective connectors 216, 218. The proximal end portion 208 of the proximal section 204 may include a similar, compatible connector 220. The connectors 216, 218, 220 may be mechanical and/or magnetic, for example. In some example embodiments, the connectors 216, 218, 220 may include generally axially slidably engageable concentric cylinders that may be retained in the engaged configuration by magnets.

Some example introducers 200 may include external markings or indicia 222, 224. For example, an orientation line 222 may indicate a circumferential position on the distal section 202 and/or the proximal section 204. The distal section 202 and/or the proximal section 204 may include sizing markings 224, which may indicate axial length (or position) along the introducer 200.

Figure 6:
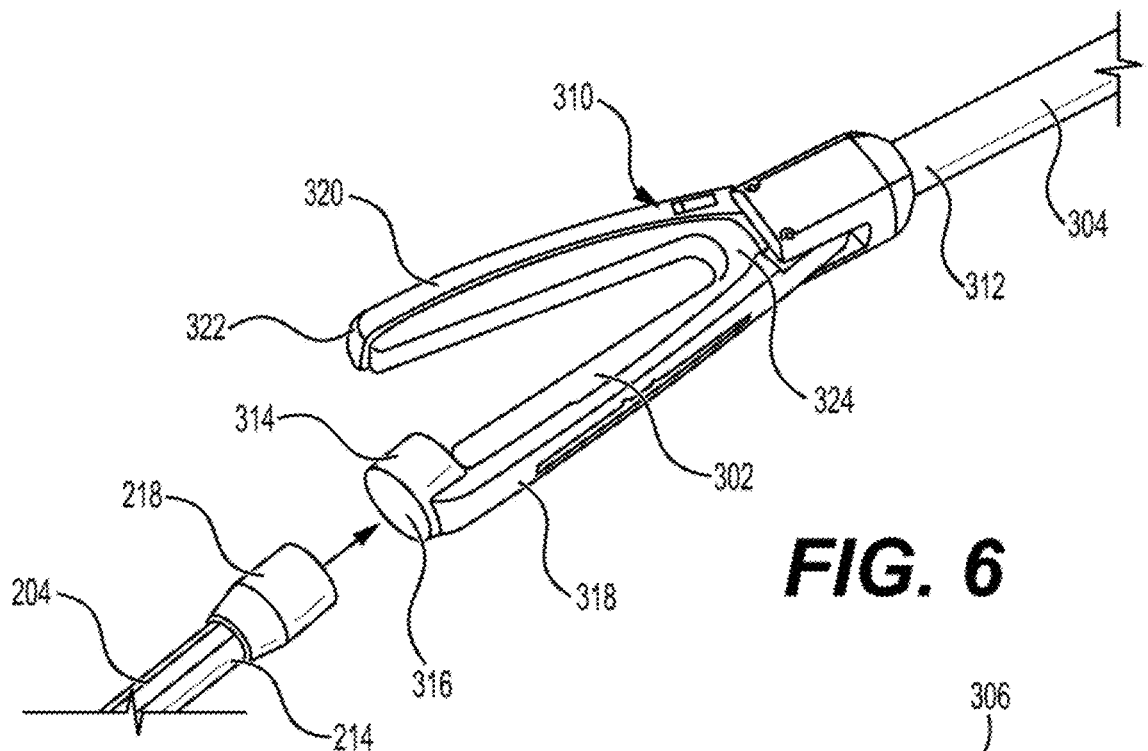
FIG. 6 is a detailed isometric view of a distal end portion of an example clip applier.
Figure 7:
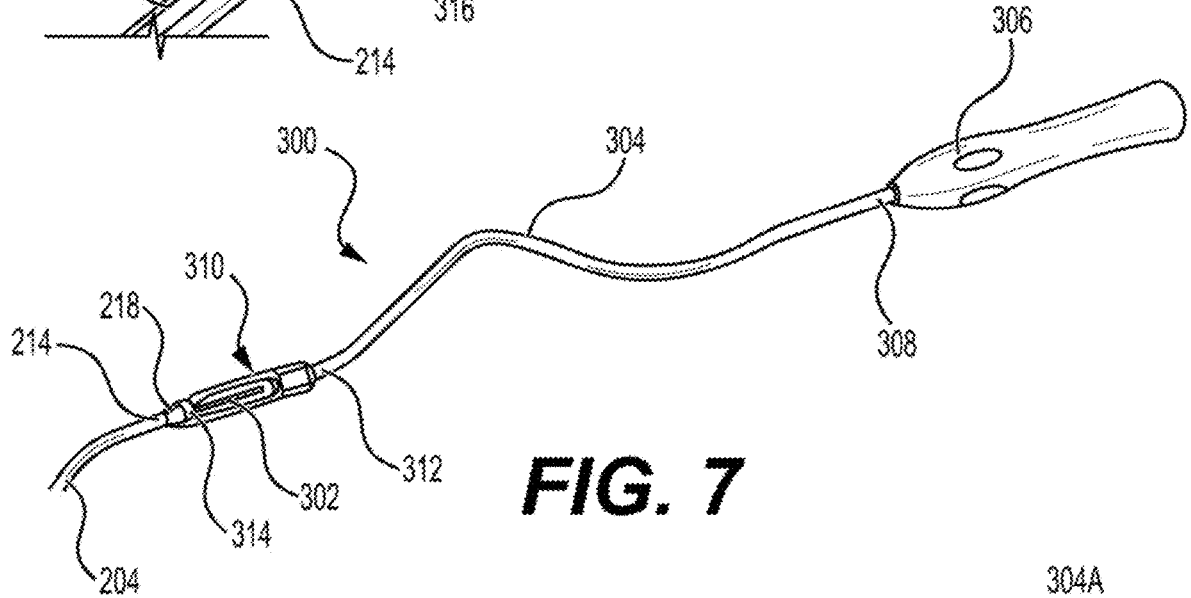
FIG. 7 is an isometric view of an example clip applier.

FIG. 6 is a detailed isometric view of a distal end portion of an example clip applier 300 and FIG. 7 is an isometric view of an example clip applier 300, according to at least some aspects of the present disclosure. Referring to FIGS. 1, 6, and 7, the clip applier 300 may include an elongated shaft 304, a handle 306 disposed at a proximal end portion 308 of the shaft 304, and/or an end effector 310 disposed at a distal end portion 312 of the shaft 304. The end effector 310 may be configured to deliver and/or apply the occlusion clip 302, such as onto the LAA 14.

In some example clip appliers 300, a distal tip portion 314, such as of the end effector 310, may be configured to releasably couple with the proximal section 204 of the introducer 200. For example, the distal tip portion 314 may include a connector 316 which may be configured to releasably couple with the connector 218 of the distal end portion 214 of the proximal section 204 of the introducer 200 and/or the connector 220 of the proximal end portion 208 of the proximal section 204 of the introducer 200 (FIG. 1). The connectors 218, 220, 316 may be mechanical and/or magnetic, for example. In some example embodiments, the connectors 218, 220, 316 may be configured to prevent relative rotation between the introducer 200 and the end effector 310. Alternatively, the connectors 218, 220, 316 may be configured to allow relative rotation between the introducer 200 and the end effector 310.

In the example embodiment illustrated in FIGS. 1, 6, and 7, the end effector 310 may include a first jaw 318 and/or a second jaw 320, one or both of which may be articulated to open and/or close the occlusion clip 302 before it is deployed. The connector 316 of the distal tip portion 314 of the clip applier 300 may be disposed on the first jaw 318, for example. A distal portion 322 of the second jaw 320 may be generally rounded to facilitate atraumatic insertion and/or positioning of the end effector 310. In some example embodiments, the distal tip portion 314 may be permanently attached to (e.g., integrally formed as a part of) the first jaw 318.

Some example occlusion clips 302 and/or clip appliers 300 may be generally similar to those described in the patent references incorporated by reference herein, and may be operated in generally similar manners. As shown in FIGS. 1, 6, and 7, an open-ended occlusion clip 302 may be preloaded into the end effector 310. Alternatively, a closed-ended occlusion clip may be utilized. The occlusion clip 302 may include a heel portion 324, which, in some example embodiments, may be generally proximally oriented when the occlusion clip 302 is disposed on the clip applier 300.

The end effector 310 may include one or more mechanisms operable to open the clip 302, lock the clip 302 open, close the clip 302, and/or deploy the clip 302, such as using one or more pulleys, wires, and/or sutures operatively coupled to an actuator disposed on the handle 306. In some example embodiments, the end effector 310 may include one or more articulation joints. The patent references incorporated by reference herein describe various suitable example mechanisms.

Figure 8:
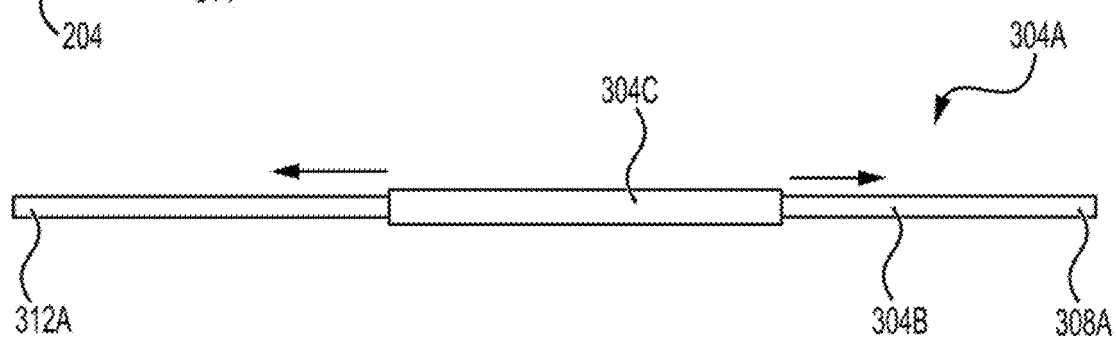
FIG. 8 is a side elevation view of an alternative example shaft of a clip applier.

The shaft 304 may be substantially rigid (e.g., generally not bendable), generally flexible, substantially malleable (e.g., plastically deformable), and/or steerable. For example, the shaft 304 may be bendable in one or more curves in one or more planes, such as shown in FIGS. 1 and 7, which may facilitate positioning of the end effector 310 and/or the occlusion clip 302. The shaft 304 may be configured to transmit torque between the handle 306 and the end effector 310, which may facilitate placement of the occlusion clip 302. In some example embodiments, the shaft 304 may include a laser-cut metal tube, which may provide both adequate flexibility and torque transmission FIG. 8 is a side elevation view of an alternative example shaft 304a of a clip applier, according to at least some aspects of the present disclosure. The shaft 304a may include a generally flexible, inner shaft 304b extending generally between a proximal end portion 308a and a distal end portion 312a. A substantially malleable (e.g., plastically deformable) outer shaft 304c, which may be substantially shorter than the inner shaft 304b, may be axially slidably disposed around the inner shaft 304b. The portion of the shaft 304a where the outer shaft 304c is positioned may be substantially more rigid than the uncovered portions of the inner shaft 304b. In use, the shaft 304a may be advanced to an operative area with the outer shaft 304c in a relatively proximal position. As such, the distal portion of the shaft 304a nearest the operative area may be generally flexible. Then, the outer shaft 304c, which may be bent by the operator into a desired shape, may be moved from the relatively proximal position to a relatively distal position. With the outer shaft 304c in the relatively distal position, the operator may be able to impart lateral forces at the distal end portion of the shaft 312a, such as to position an end effector carrying an occlusion device on an anatomic structure.

Figure 9:
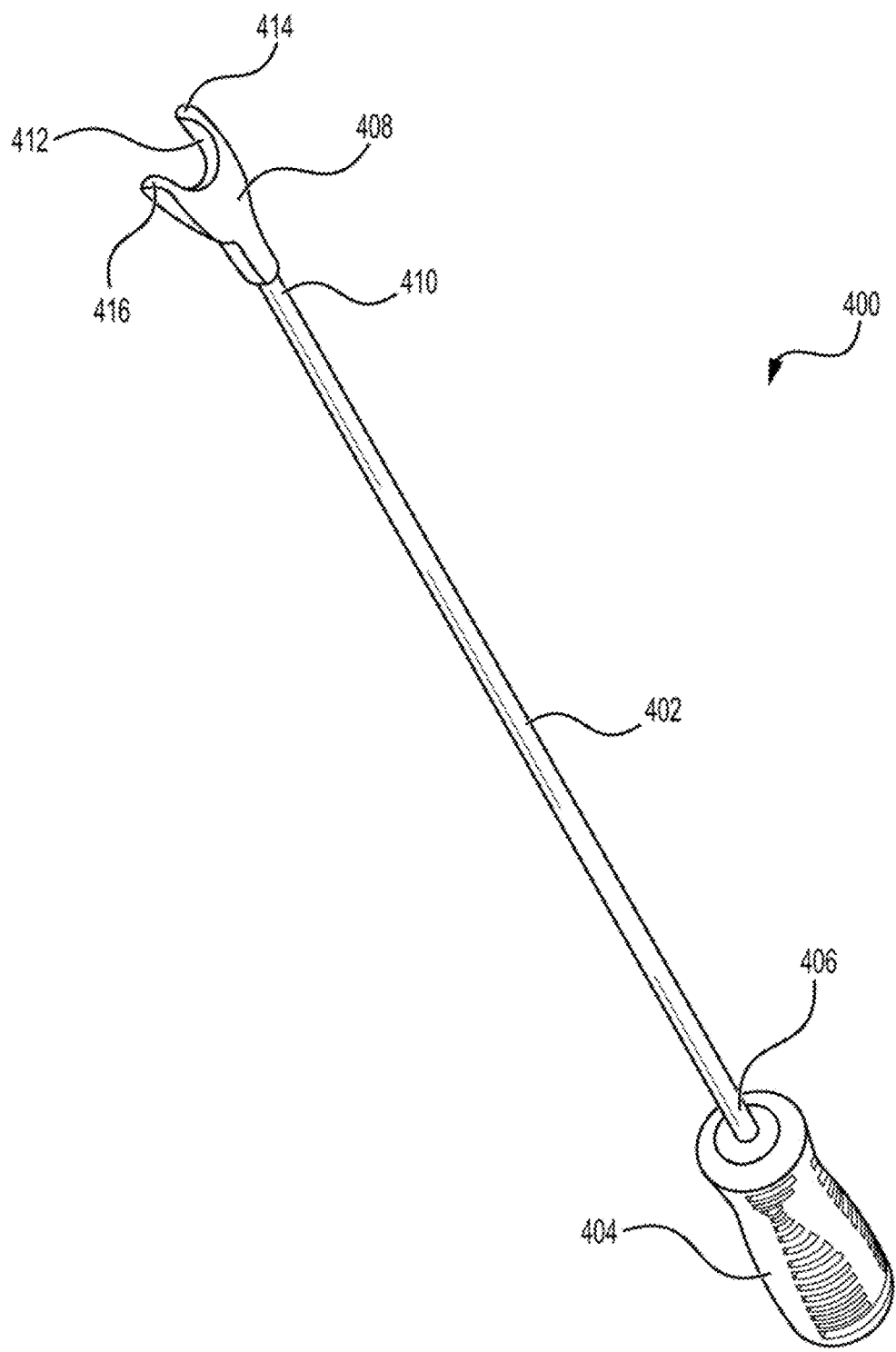
FIG. 9 is an isometric view of an example positioner.

FIG. 9 is an isometric view of an example positioner 400, according to at least some aspects of the present disclosure. The positioner 400 may include an elongated, substantially rigid shaft 402, a handle 404 disposed at a proximal end portion 406 of the shaft 402, and/or a head 408 disposed at a distal end portion 410 of the shaft. Generally, the head 408 may be configured to apply linear and/or torsional forces to other components of the clip application system 10 and/or a patient's anatomical structures. For example, the head 408 may include a generally U-shaped engaging portion 412, which may include a distally facing opening and/or which may include two generally rounded, distal tips 414, 416.

Referring to FIGS. 1 and 6, as described above, the distal tip portion 314 of the clip applier 300 may be configured to releasably couple with the proximal section 204 of the introducer 200. Specifically, the connector 218 of the distal end portion 214 of the proximal section 204 of the introducer may be configured to releasably couple with the connector 316 of the distal tip portion 314 of the clip applier 300. This example connection may be detached merely by pulling apart the introducer 200 and the clip applier 300. The present disclosure contemplates that, in some circumstances, it may be advantageous to employ an alternative connection between the distal tip portion 314 of the clip applier 300 and the proximal section 204 of the introducer 200. For example, in some circumstances, it may be advantageous to utilize a connection between the distal tip portion 314 of the clip applier 300 and the proximal section 204 of the introducer 200 that, once connected, may not be readily detachable merely by applying tension to the introducer 200 and the clip applier 300. In some circumstances, it may desirable to utilize a connection between the distal tip portion 314 of the clip applier 300 and the proximal section 204 of the introducer 200 that may be detachable only when an actuator on the handle 306 of the clip applier 300 is operated, such as to deploy the occlusion clip 302. Referring to FIGS. 1, 4, and 5, in some circumstances, it may be desirable for the connections between the distal section 202 and proximal section 204 of the introducer 200 to releasably couple in a manner that may not be detachable merely by applying tension to the distal section 202 and the proximal section 204. It may be desirable to utilize connectors, such as the connectors described below, which, unless unlocked (e.g., by pressing a button or rotating the connectors) are secured together (e.g., locked) to resist separation by merely being pulled apart.

Figure 10:
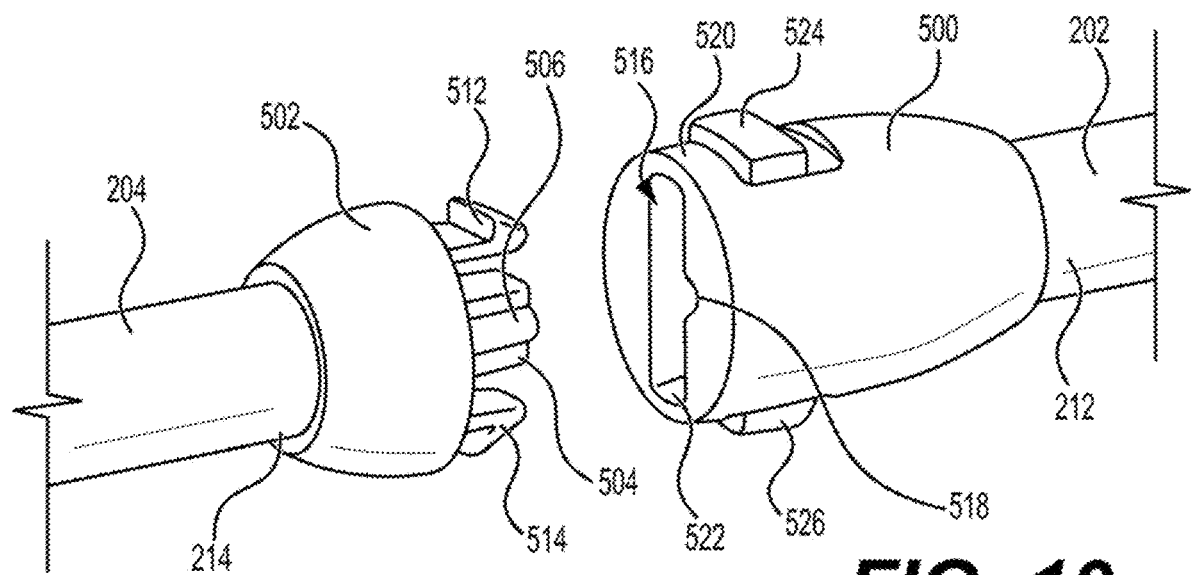
FIGS. 10-12 are detailed isometric view of alternative example connectors configured to couple a distal section and a proximal section of an introducer.
Figure 11:
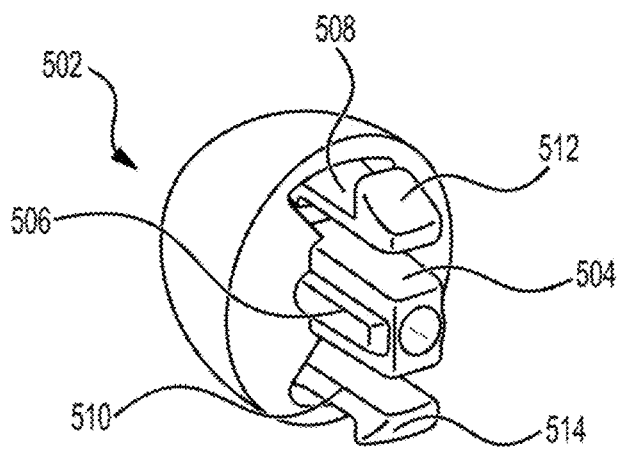
Figure 12:
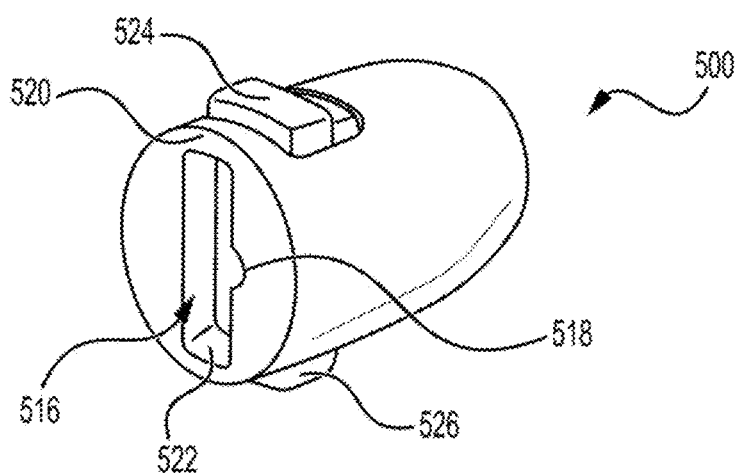
Figure 13:
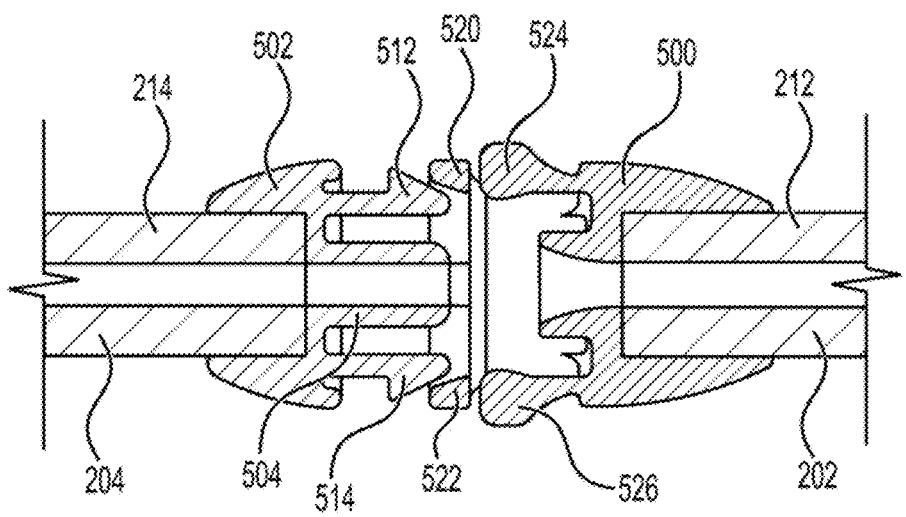
FIGS. 13 and 14 are longitudinal cross-sectional views of alternative example connectors configured to couple a distal section and a proximal section of an introducer.
Figure 14:
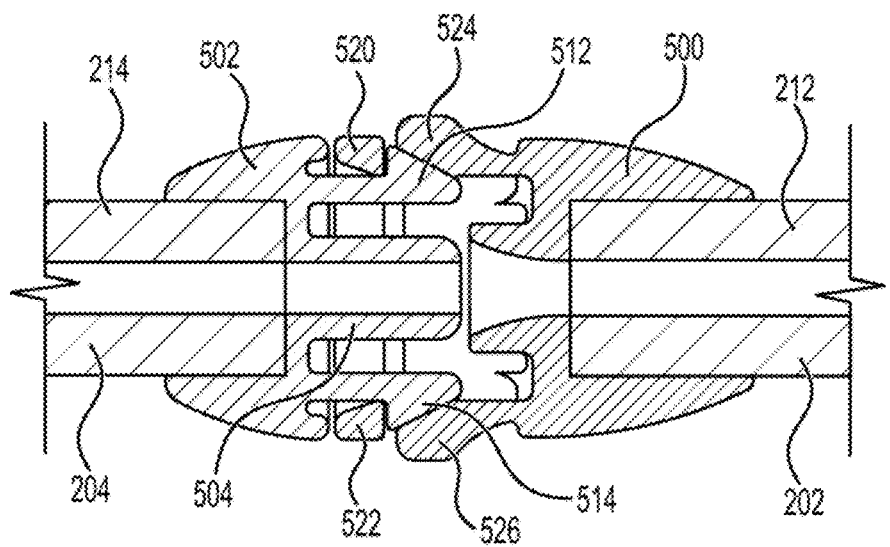
Figure 15:
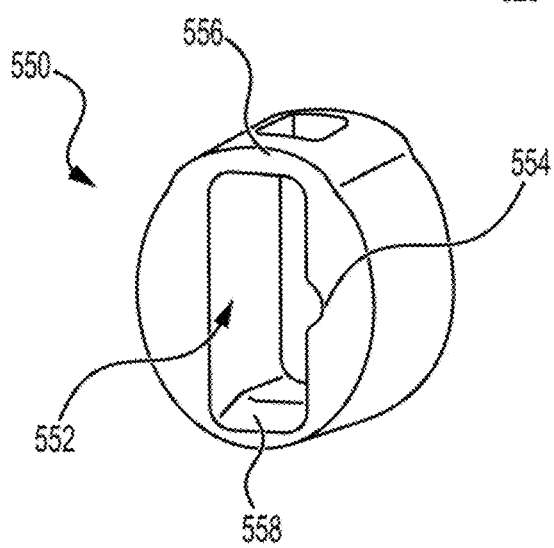
FIG. 15 is a detailed isometric view of an alternative example connector for a clip applier.

FIGS. 10-12 are detailed isometric view of alternative example connectors 500, 502 configured to couple the distal section 202 and the proximal section 204 of the introducer 200, FIGS. 13 and 14 are longitudinal cross-sectional views of alternative example connectors configured to couple the distal section 202 and the proximal section 204 of the introducer 200, and FIG. 15 is a detailed isometric view of an alternative example connector 550 for a clip applier 300, according to at least some aspects of the present disclosure.

Referring to FIGS. 10-14, the proximal end portion 212 of the distal section 202 of the introducer 200 may be configured to releasably couple to the distal end portion 214 of the proximal section 204 of the introducer 200, such as by respective connectors 500, 502. The connector 502 of the proximal section 204 may include a longitudinally projecting post 504, which may extend generally along the central axis of the proximal section 204. The post 504 may include an orientation feature, such as a lateral projection 506. The connector 502 may include one or more longitudinally projecting arms 508, 510, which may include respective latches 512, 514.

The connector 500 of the distal section 202 may include an opening 516 configured to receive components of the connector 502 therein. The opening 516 may include an orientation feature, such as a groove 518, which may be configured to engage the orientation feature of the connector 502 (e.g., the projection 506) so that the connectors 500, 502 are connectable only in one or more desired, known relative orientation(s). The connector 500 may include one or more flanges 520, 522 configured to engage the latches 512, 514 of the connector 502, respectively.

In this example embodiment, when the connectors 500, 502 are connected, the latches 512, 514 slide on the radially inwardly facing surface of the flanges 520, 522, elastically deflecting the arms 508, 510, until the latches 512, 514 pass axially beyond the flanges 520, 522. Then, the latches move radially outward, engaging the latches 512, 514 with the flanges 520, 522 to prevent the connectors 500, 502 from separating. To release the latches 512, 514 from the flanges 520, 522, a user may press radially inward on the outwardly projecting buttons 524, 526, which may be arranged to press the latches 512, 514 radially inward so that they may disengage and move past the flanges 520, 522.

Referring to FIG. 15, the connector 550 of the distal tip portion 314 of the clip applier 550 may be generally similar to the connector 500 of the distal section 202 of the introducer 200. The connector 550 may include an opening 552 configured to receive components of the connector 502 therein. The opening 552 may include an orientation feature, such as a groove 554, which may be configured to engage the orientation feature of the connector 502 (e.g., the projection 506) so that the connector 502, 550 are connectable only in one or more desired, known relative orientation(s). The connector 550 may include one or more flanges 556, 558 configured to engage the latches 512, 514 of the connector 502, respectively. When the connectors 502, 550 are connected, the latches 512, 514 may slide on the radially inwardly facing surfaces of the flanges 556, 558 (elastically deflecting the arms 508, 510) until the latches 512, 514 pass axially beyond the flanges 556, 558. Then, the latches may move radially outward, engaging the latches 512, 514 with the flanges 556, 558 to prevent the connectors 502, 550 from separating. In the example embodiment illustrated in FIG. 15, the connector 550 may not include buttons corresponding to buttons 524, 526 of connector 500. Accordingly, under normal use, the connectors 502, 550 may not be readily separable once they have been connected.

Figure 16:
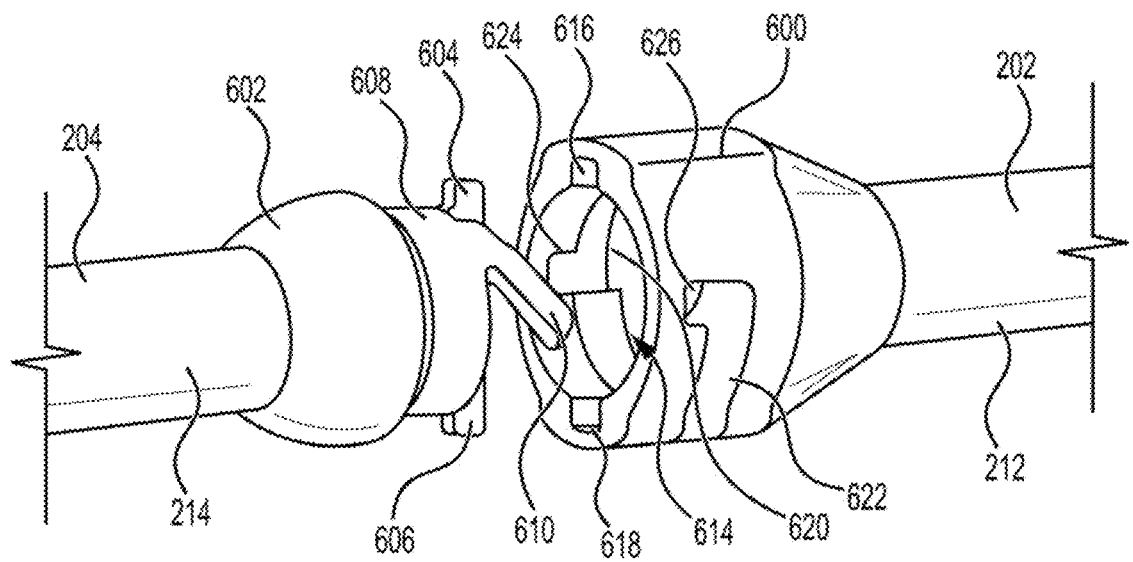
FIGS. 16-18 are detailed isometric view of alternative example connectors configured to couple a distal section and a proximal section of an introducer.
Figure 17:
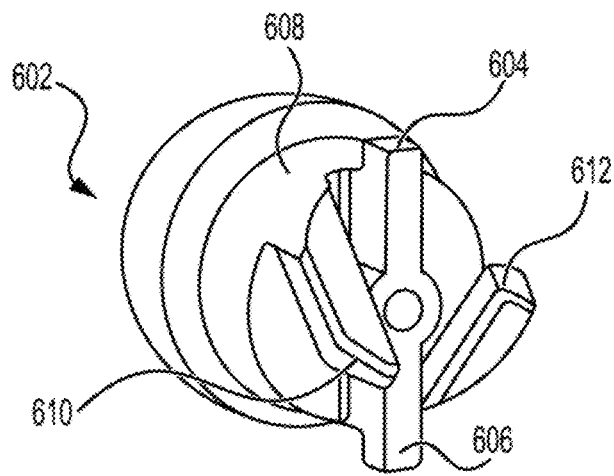
Figure 18:
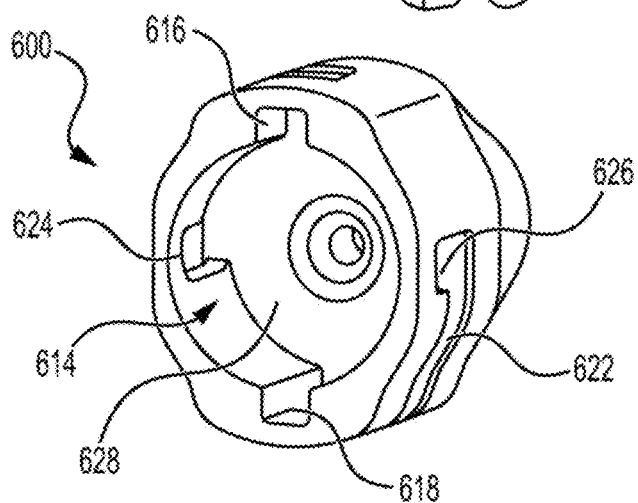
Figure 19:
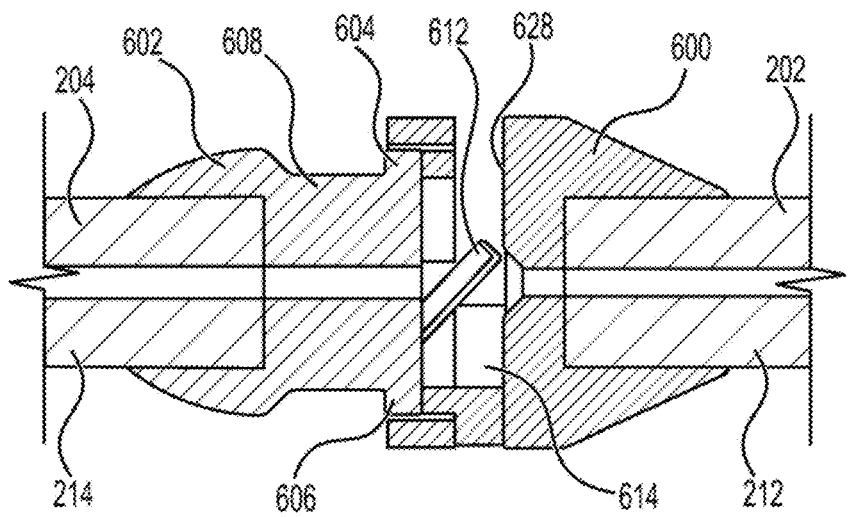
FIGS. 19 and 20 are longitudinal cross-sectional views of alternative example connectors configured to couple a distal section and a proximal section of an introducer.
Figure 20:
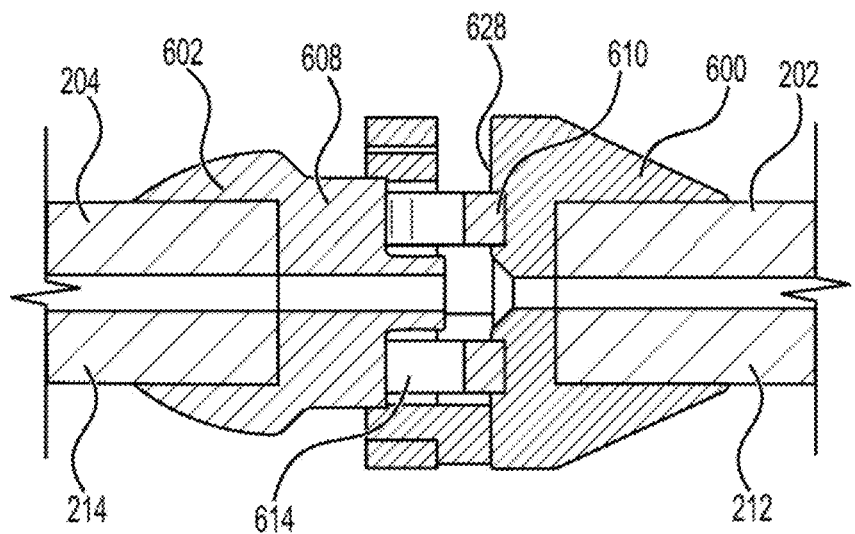
Figure 21:
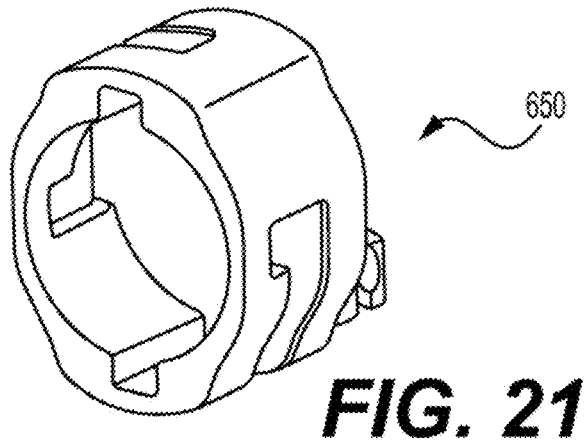
FIG. 21 is a detailed isometric view of an alternative example connector for a clip applier.

FIGS. 16-18 are detailed isometric view of alternative example connectors 600, 602 configured to couple the distal section 202 and the proximal section 204 of the introducer 200, FIGS. 19 and 20 are longitudinal cross-sectional views of alternative example connectors 600, 602 configured to couple the distal section 202 and the proximal section 204 of the introducer 200, and FIG. 21 is a detailed isometric view of an alternative example connector 650 for a clip applier 300, according to at least some aspects of the present disclosure.

Referring to FIGS. 16-20, the proximal end portion 212 of the distal section 202 of the introducer 200 may be configured to releasably couple to the distal end portion 214 of the proximal section 204 of the introducer 200, such as by respective connectors 600, 602. The connector 602 of the proximal section 204 may include one or more radial projections 604, 606, which may extend radially outward from a generally cylindrical, central boss 608. The connector 602 may include one or more spring arms 610, 612, which may extend longitudinally from the central boss 608, such as diagonally.

The connector 600 of the distal section 202 may include an opening 614 configured to receive components of the connector 602 therein. The connector 600 may include one or more generally longitudinal entry slots 616, 618 configured to receive projections 604, 606, respectively. The entry slots 616, 618 may connect to respective, generally circumferential rotation slots 620, 622. The rotation slots 620, 622 may connect to respective, generally longitudinal locking slots 624, 626. The connector 600 may include a generally axially facing surface 628, which may be configured to engage the spring arms 610, 612 of the connector 602.

In this example embodiment, when the connectors 600, 602 are connected, the radial projections 604, 606 may slide longitudinally in the entry slots 616, 618. As the projections 604, 606 slide in the entry slots 616, 618, the spring arms 610, 612 may contact the surface 628, which may cause the spring arms 610, 612 to elastically deflect. Then, the connector 602 may be rotated with respect to the connector 600, which may cause the projections 604, 606 to slide circumferentially in the rotation slots 620, 622. When the projections 604, 606 are aligned with the locking slots 624, 626, the longitudinally separating force due to the deformed spring arms 610, 612 may cause the projections 604, 606 to slide longitudinally into the dead-end locking slots 624, 626. The separating force may retain the projections 604, 606 in the locking slots 624, 626. Once the projections 604, 606 are engaged in the locking slots 624, 626, the connectors may remain connected until the connector 602 is moved longitudinally towards the connector 600, deflecting the spring arms 610, 612, to align the projections 604, 606 circumferentially with the rotation slots 620, 622, allowing rotation of the connector 602 with respect to the connector 600. When the projections 604, 606 are aligned with the entry slots 616, 618, the connectors 600, 602 may be separated.

Referring to FIG. 21, the connector 650 of the distal tip portion 314 of the clip applier 550 may be substantially similar to the connector 600 of the distal section 202 of the introducer 200 in construction and operation. Accordingly, repeated description is omitted for brevity.

Figure 22:
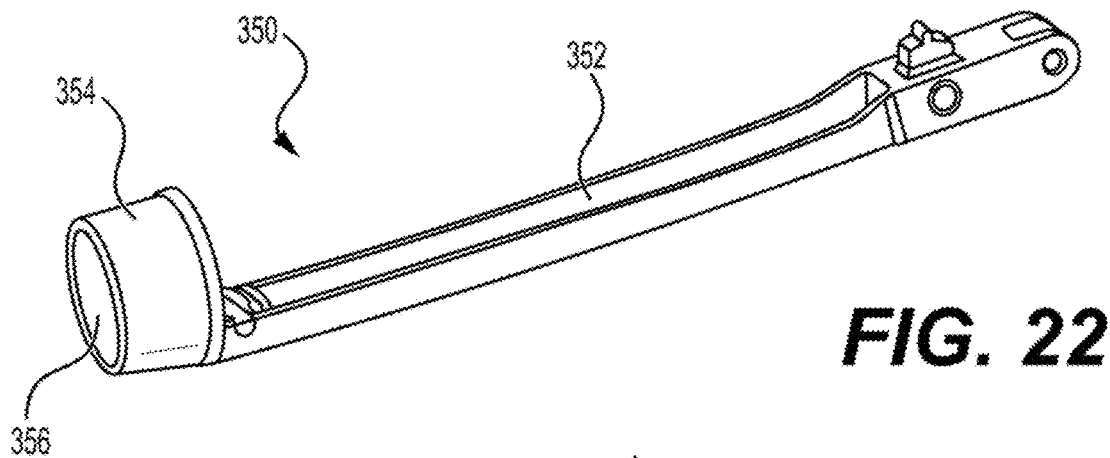
FIG. 22 is an isometric view of an alternative example first jaw.
Figure 23:
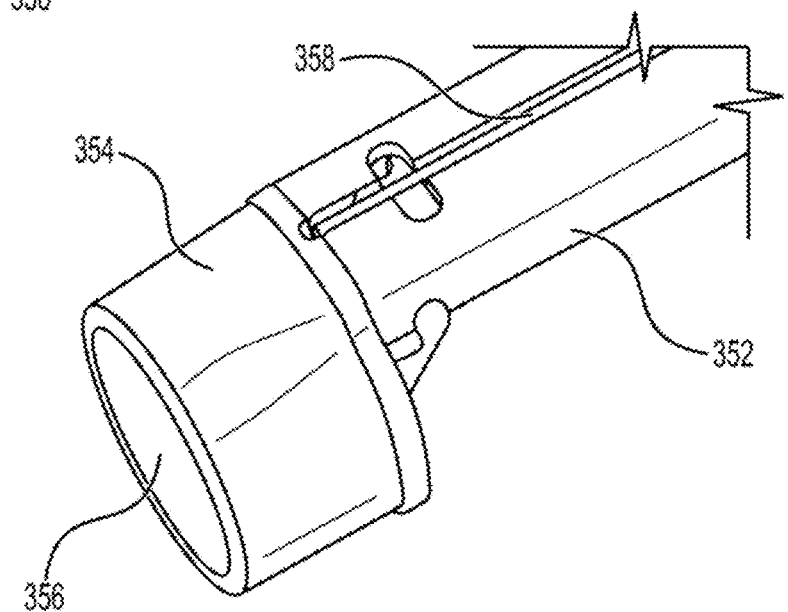
FIG. 23 is a detailed isometric view of an alternative example first jaw.
Figure 24:
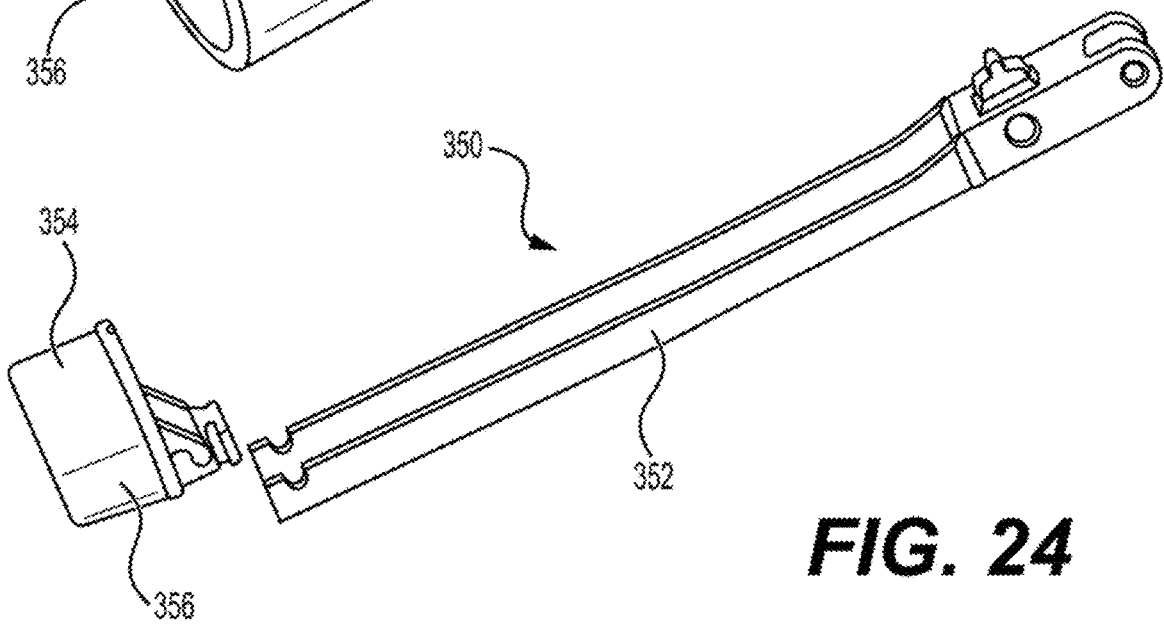
FIG. 24 is an exploded isometric view of an alternative example first jaw.

FIG. 22 is an isometric view of an alternative example first jaw 350, FIG. 23 is a detailed isometric view of an alternative example first jaw 350, and FIG. 24 is an exploded isometric view of an alternative example first jaw 350, according to at least some aspects of the present disclosure. Referring to FIGS. 22-24, the alternative first jaw 350 is generally similar to and/or may be substituted for the first jaw 318 described above in various clip appliers 300 according to at least some aspects of the present disclosure.

The first jaw 350 may include an assembly of a jaw member 352 and/or a releasably attached distal tip portion 354. The jaw member 352 may be configured to releasably hold a portion of the occlusion clip 302 (FIG. 6). The distal tip portion 354 may include a connector 356, which may be generally similar in structure and/or function to any of the connectors 316, 550, 650 described herein. The distal tip portion 354 may be releasably attached to the jaw member 352, such as by a slidable wire 358. The wire 358 may be constructed from suture material, metal wire, or other similar material. For example, when the wire 358 is in the distal position as shown in FIG. 23, the wire 358 may prevent the distal tip portion 354 from detaching from the jaw member 352. When the wire 358 is withdrawn proximally, such as by operation of an actuator on the handle 306 of the clip applier 300, the distal tip portion 354 may be separable from the jaw member 352 as shown in FIG. 24.

Although a releasably attached distal tip portion 354 may be utilized in various example embodiments according to at least some aspects of the present disclosure, a clip applier 300 including a releasably attached distal tip portion 354 may be advantageously used in connection with embodiments including a connection between the distal tip portion 314 of the clip applier 300 and the proximal section 204 of the introducer 200 that, once connected, is not readily detachable merely by pulling apart the introducer 200 and the clip applier 300.

FIGS. 25-33 are anterior perspective views of a heart 12 illustrating an example method of using a clip application system 10 to apply an occlusion clip 302 on a LAA 14, according to at least some aspects of the present disclosure. In some example LAA 14 exclusion procedures utilizing the clip application system 10, access to the patient's heart 12 may be obtained via a sub-xiphoid or sub-costal incision. Some example clip application systems 10 may be utilized in connection with ablation procedures for treating atrial fibrillation. For example, the clip application system 10 may be used to exclude the LAA 14 as described below following an ablation procedure, which may utilize the EPi-Sense Guided Coagulation System available from AtriCure, Inc. of Mason, Ohio.

Figure 25:
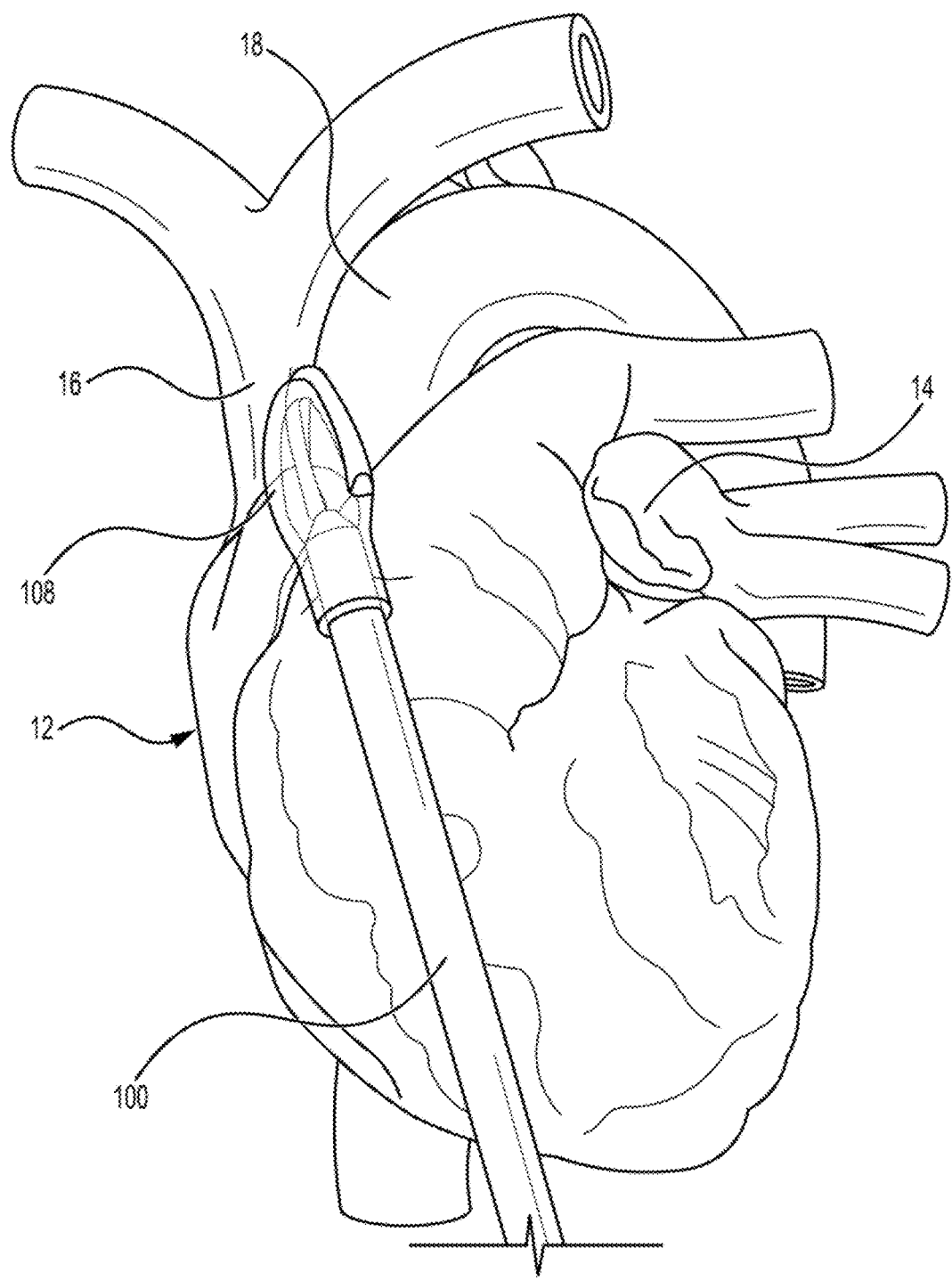
FIGS. 25-33 are anterior perspective views of a heart illustrating an example method of using a clip application system to apply an occlusion clip on a left atrial appendage; all in accordance with at least some aspects of the present disclosure.

Referring to FIG. 25, the visualization tool 100 may be advanced through the sub-xiphoid or sub-costal incision and positioned with the scope hood 108 proximate the right, anterior portion of the heart 12 so that the transverse sinus entrance (e.g., between the superior vena cava 16 and the aorta 18) may be visible using the scope 116 (FIG. 2).

Figure 26:
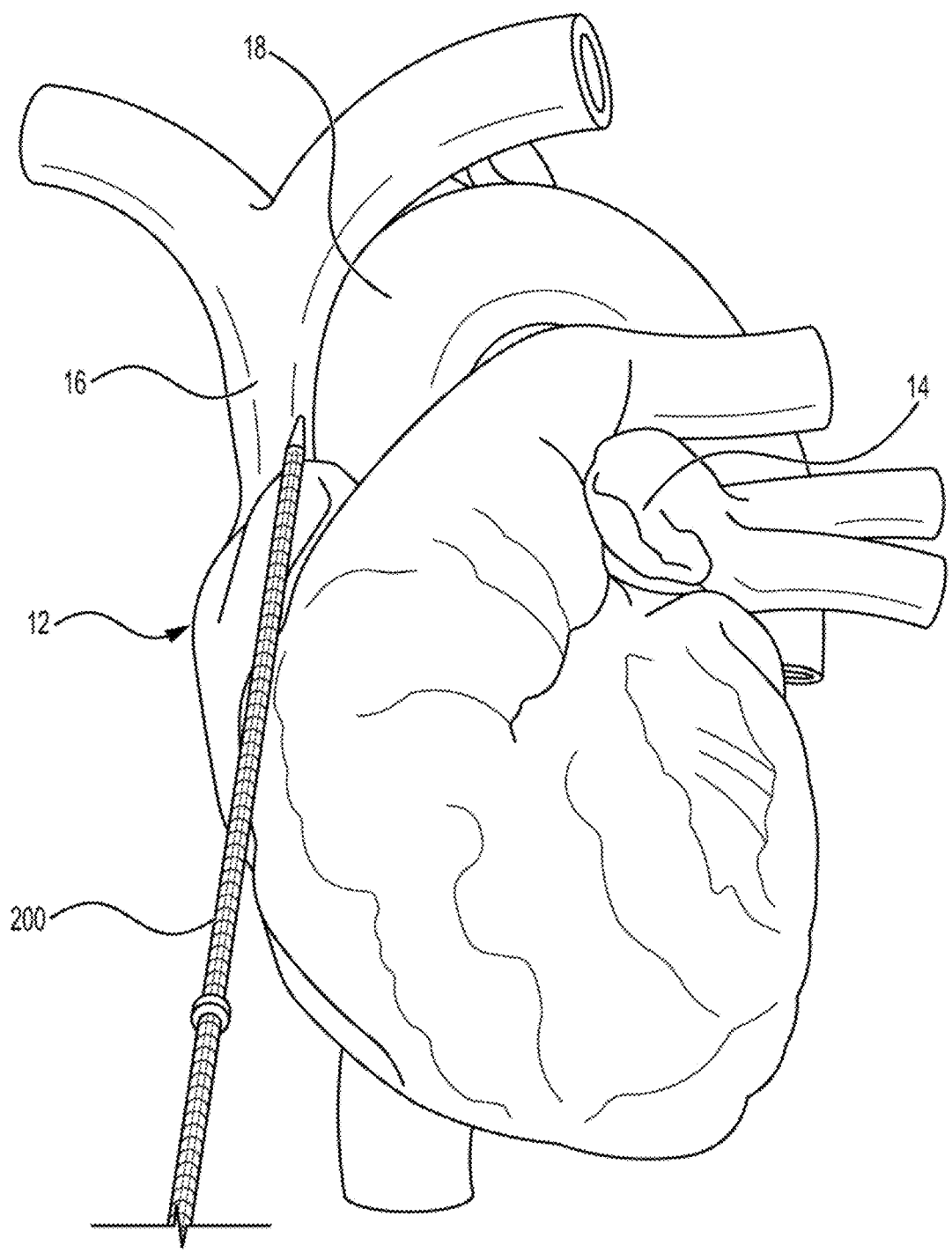

Referring to FIG. 26, the introducer 200 may be advanced into the transverse sinus opening (e.g., anterior to the superior vena cava 16 and posterior to the aorta 18). The introducer 200 may be advanced under visual guidance via the visualization tool 100. In some example embodiments, the introducer 200 may be advanced through the working channel 112 of the visualization tool 100 (not shown for clarity), and the introducer 200 may extend out of the scope hood 108 and through the lateral opening 120 (FIG. 2). Alternatively, the introducer 200 may be advanced through a cannula, sheath, or catheter, which may be positioned to direct the introducer 200 into the transverse sinus opening.

Figure 27:
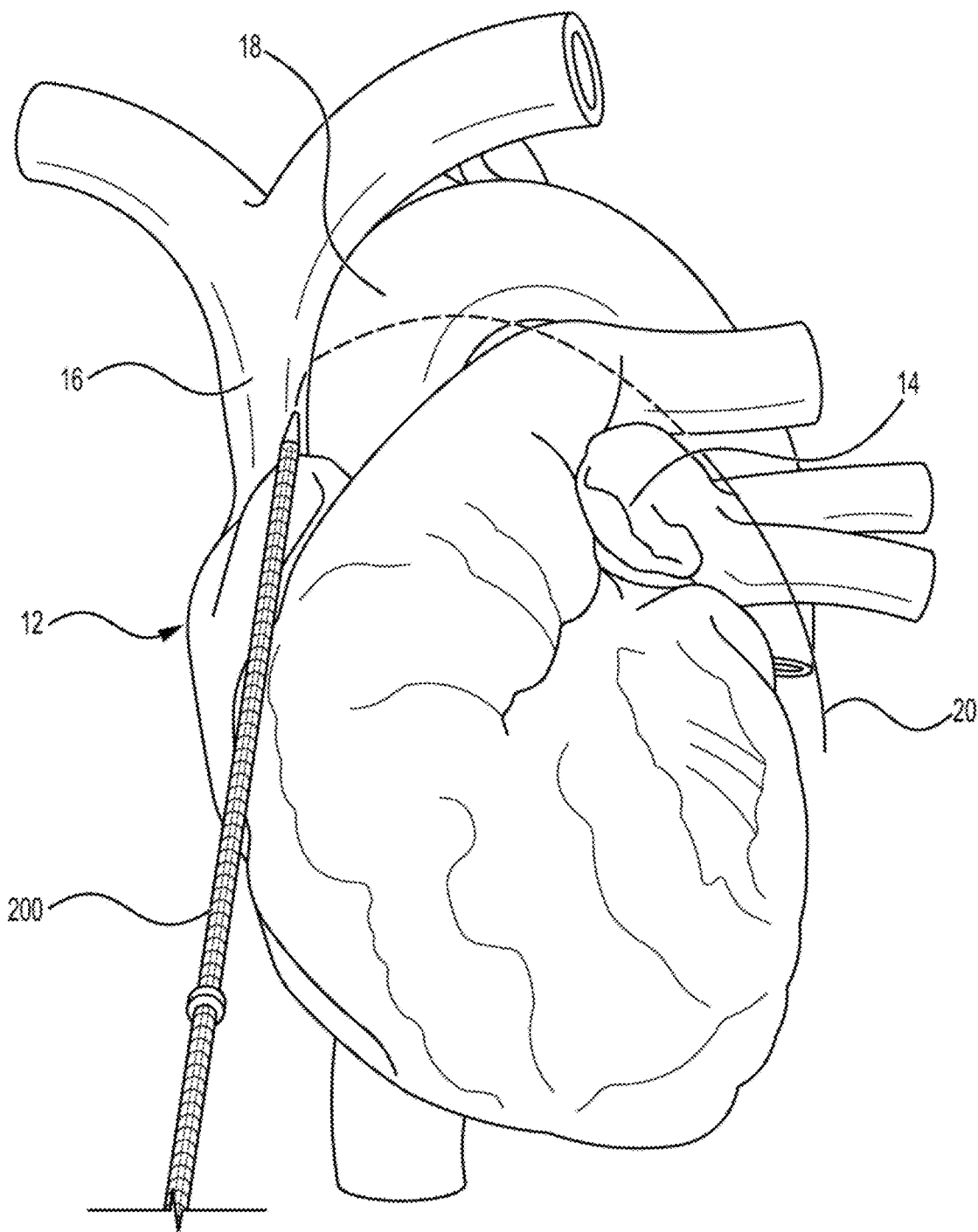

Referring to FIG. 27, optionally, a guidewire 20 may be advanced through the transverse sinus and/or out of the transverse sinus on the left side of the heart 12, such as lateral to the LAA 14. In some example embodiments, the guidewire 20 may be advanced before advancing the introducer 200. In some example embodiments, the guidewire 20 may be advanced through the lumen 206 (FIG. 5) of the introducer 200. In some example embodiments, the guidewire 20 may be advanced through the working channel 112 of the visualization tool 100 to place the guidewire 20 into the transverse sinus. Then, the visualization tool 100 may be removed over the guidewire 20. Then, the introducer 200 may be advanced over the guidewire 20 and through the transverse sinus. In some example embodiments, the guidewire 20 may be utilized in connection with a guide catheter and/or a guide sheath (not shown for clarity).

Figure 28:
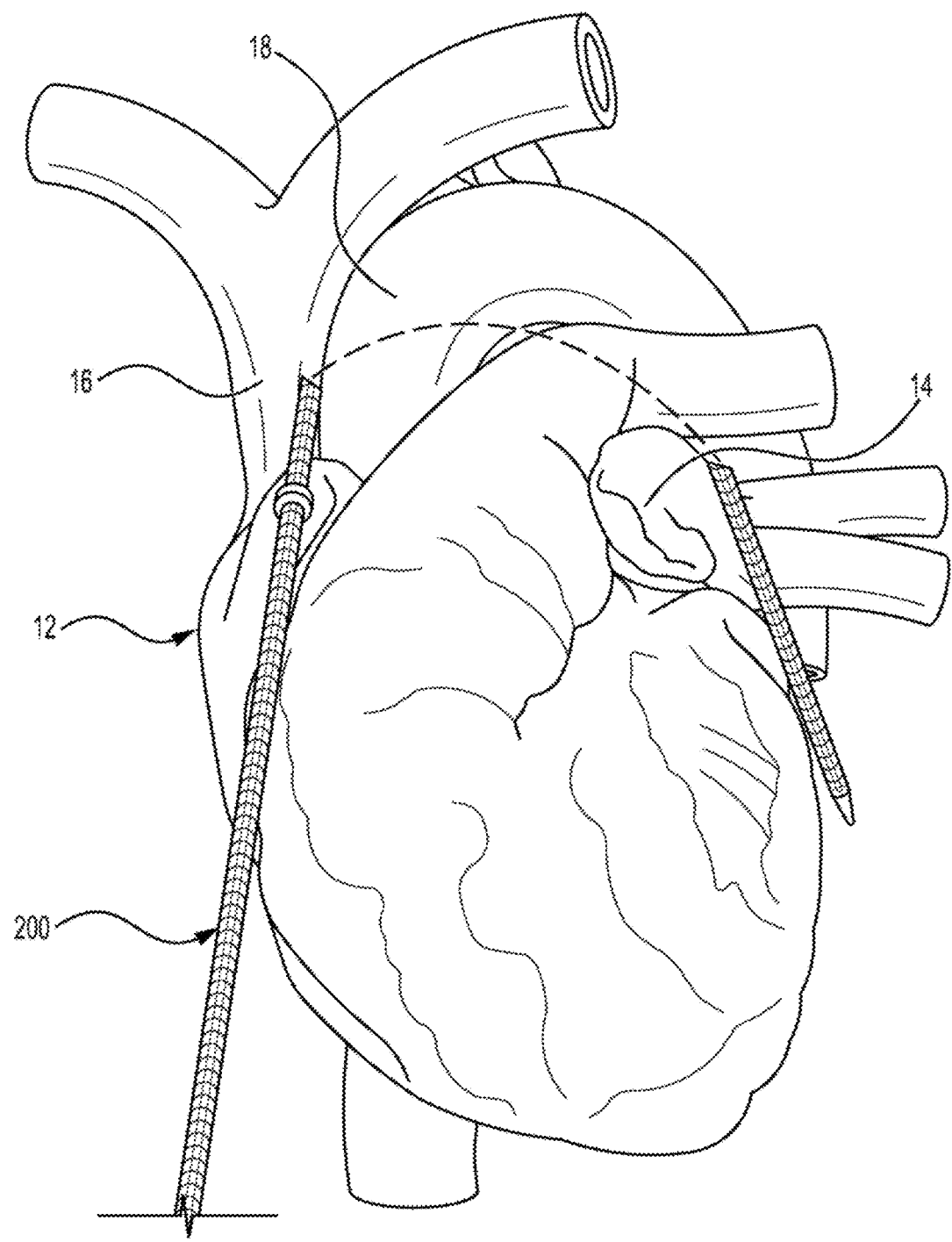

Referring to FIG. 28, the introducer 200 may be advanced through the transverse sinus and/or out of the transverse sinus on the left side of the heart 12, such as lateral to the LAA 14. If a guidewire 20 was utilized as described in connection with FIG. 27, the introducer 200 may be advanced along the previously placed guidewire 20 and/or the guidewire 20 may be removed. If the guidewire 20 was not utilized as described in connection with FIG. 27, the introducer 200 may be advanced alone. If the visualization tool 100 was used to deliver the introducer 200 and/or the guidewire 20, the visualization tool 100 may be removed over the introducer 200 and/or guidewire (leaving the introducer 200 and/or guidewire in place) after the introducer 200 enters the transverse sinus on the right side of the heart 12. The visualization tool 100 may be reinserted (without the introducer 200 and/or guidewire 20 in the channel 112) on the left side of the transverse sinus to visualize the introducer 200 exiting from the left side of the transverse sinus. The sizing markings 224 on the introducer 200 may be used to determine the size of the occlusion clip 302 that will be placed on the LAA 14, such as by measuring the width of the LAA 14.

Figure 29:
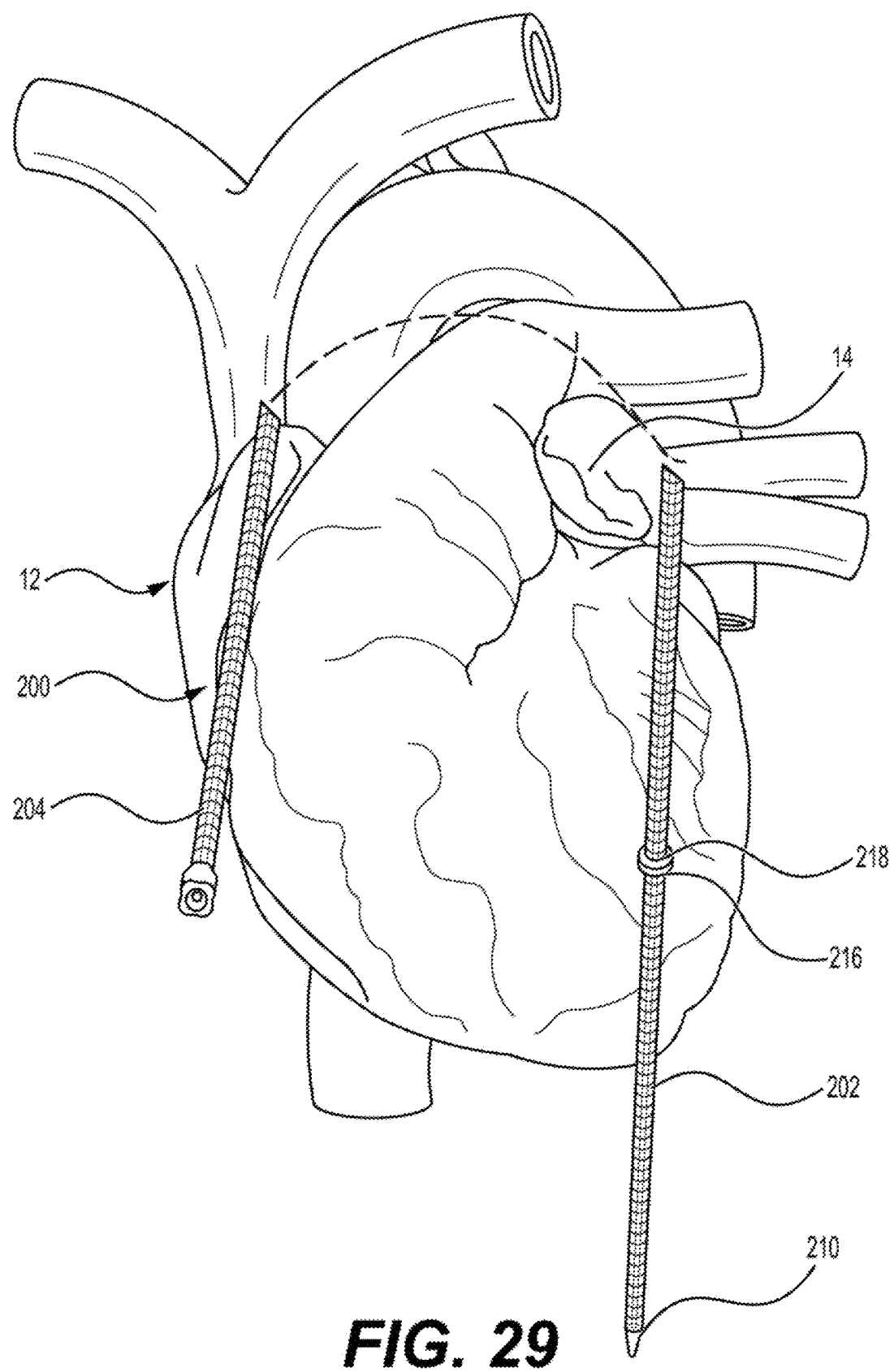

Referring to FIG. 29, the introducer 200 may be further advanced until the distal end portion 210 of the distal section 202 extends out through the sub-xiphoid or sub-costal incision or a lateral drain site incision. The introducer 200 may be further advanced until the connectors 216, 218, 500, 502, 600, 602 coupling the distal section 202 and the proximal section 204 extend out through the sub-xiphoid or sub-costal incision or a lateral drain site incision.

Figure 30:
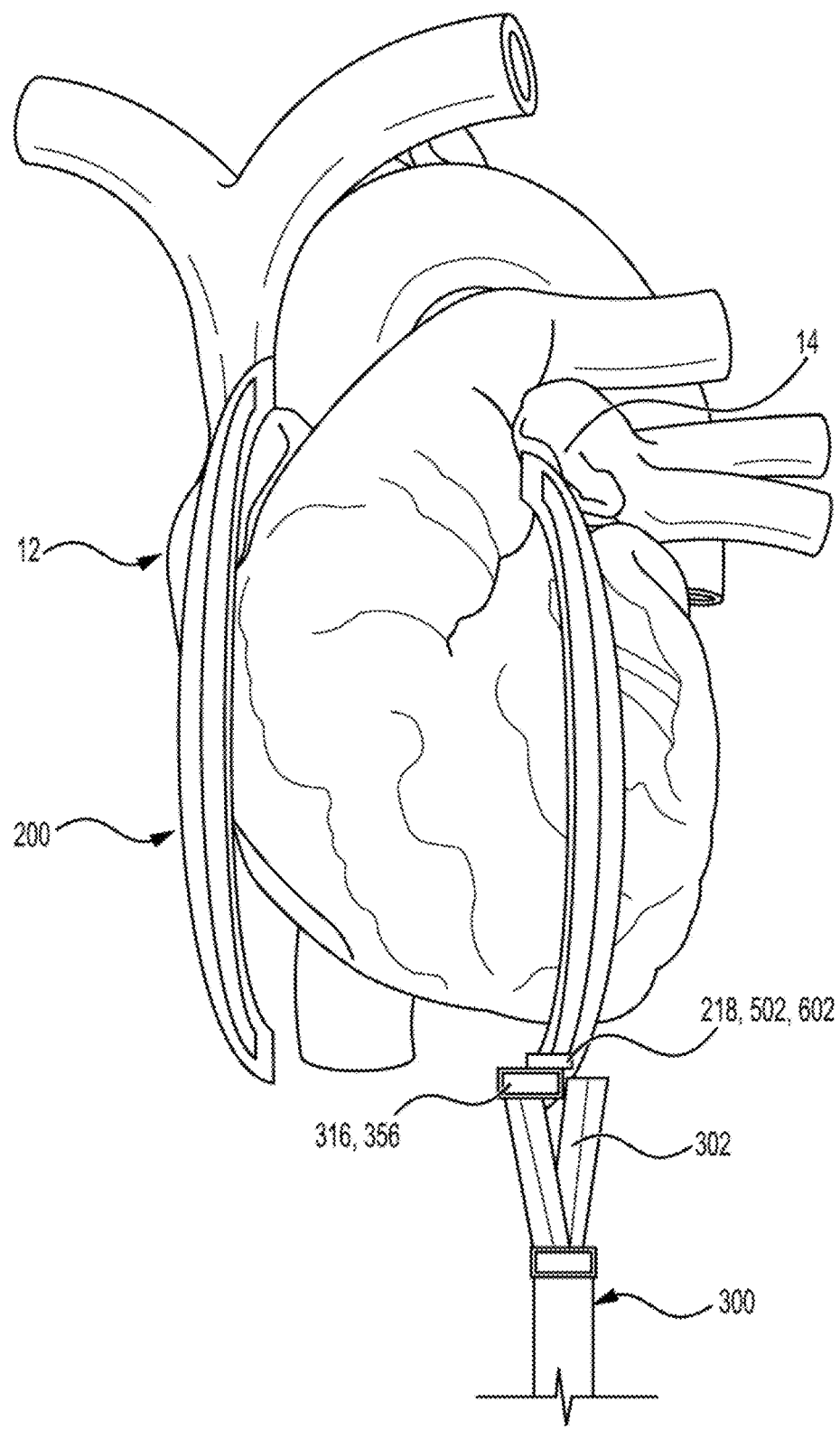

Referring to FIG. 30, the distal section 202 of the introducer 200 may be removed by disconnecting the connectors 216, 218, 500, 502, 600, 602. The clip applier 300, carrying the occlusion clip 302, may be connected to the introducer 200 by connecting the connectors 218, 316, 356, 502, 602. The orientation line 222 on the introducer 200 may be oriented toward the midline of the patient. When the clip applier 300 is connected to the introducer 200, a corresponding orientation mark on the clip applier 300 may be aligned with the orientation line 222 on the introducer 200 to help facilitate the desired orientation of the clip applier 300 jaws 318, 320 with respect to the LAA 14 when the clip applier 300 approaches the LAA 14. In some circumstances, it may be desirable for the tethered first jaw 318 (which may be coupled to the introducer 200) to be on the medial side of the LAA 14 and/or the non-tethered side to be on the lateral side of the LAA 14.

Figure 31:
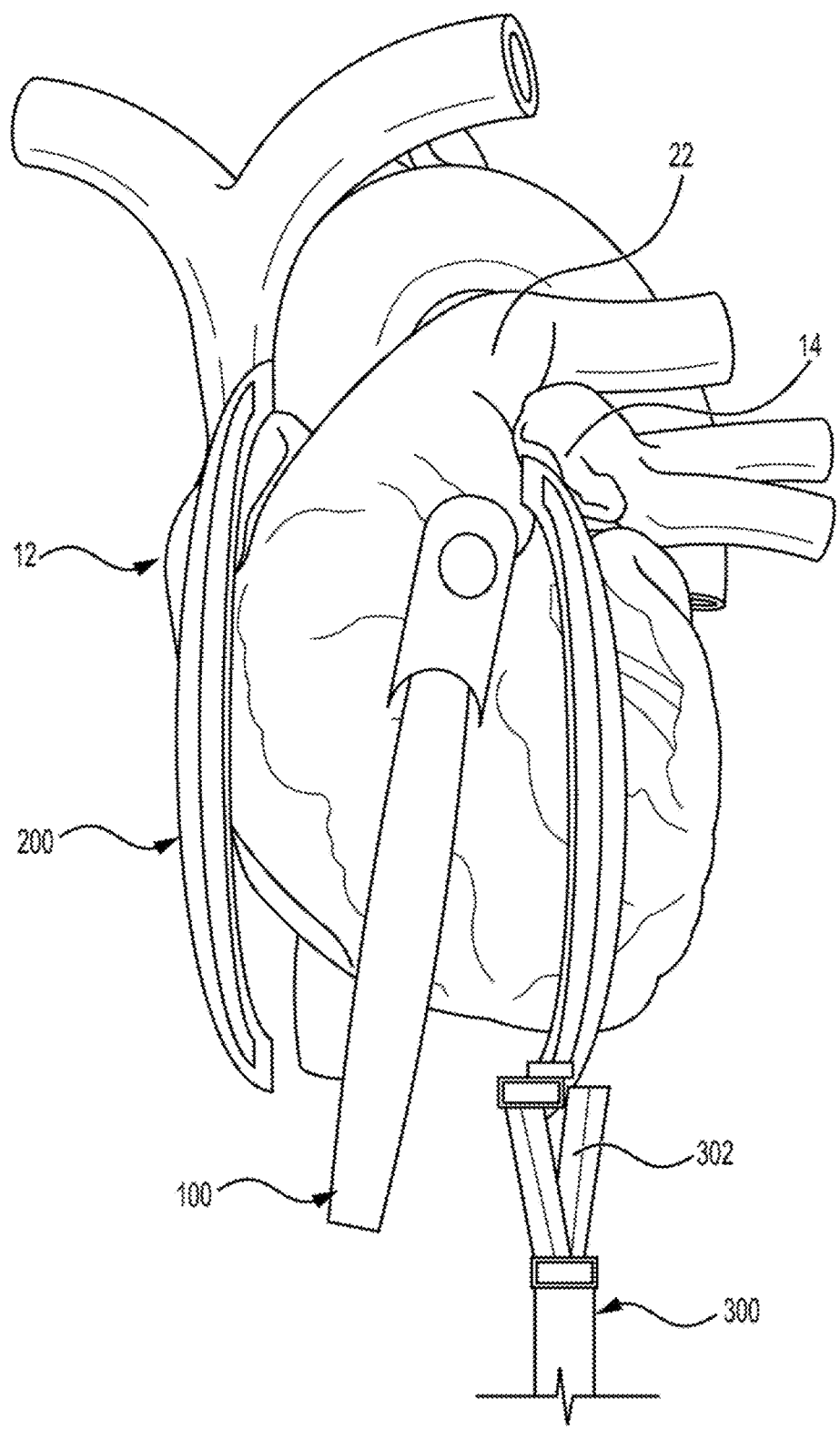

Referring to FIG. 31, the visualization tool 100 may be positioned generally on the left, anterior side of the heart to facilitate visualization of the clip applier 300 as it is advanced to the LAA 14, such as by pushing the clip applier 300 and/or pulling the introducer 200. If the clip applier 300 comprises a malleable shaft 304, the shaft 304 may be bent prior to insertion through the incision. If the introducer 200 extends out of the transverse sinus on the lateral side of the LAA 14 (as shown in FIG. 14), tensioning the introducer 200 may cause the introducer 200 to move to the medial side of the LAA 14. If the introducer 200 extends out of the transverse sinus transverse sinus on the medial side of the LAA 14, the introducer 200 may remain on the medial side of the LAA 14 as the introducer 200 is tensioned. Generally, in some example embodiments, positioning the introducer 200 on the medial side of the LAA 14 may facilitate orientation of the end effector 310 so that the second (free) jaw 320 is on the lateral side of the LAA 14. This may aid in reducing the risk of tissue damage, such as to the pulmonary artery 22, by the second jaw 320 as the clip applier 300 is positioned on the LAA 14.

Figure 32:
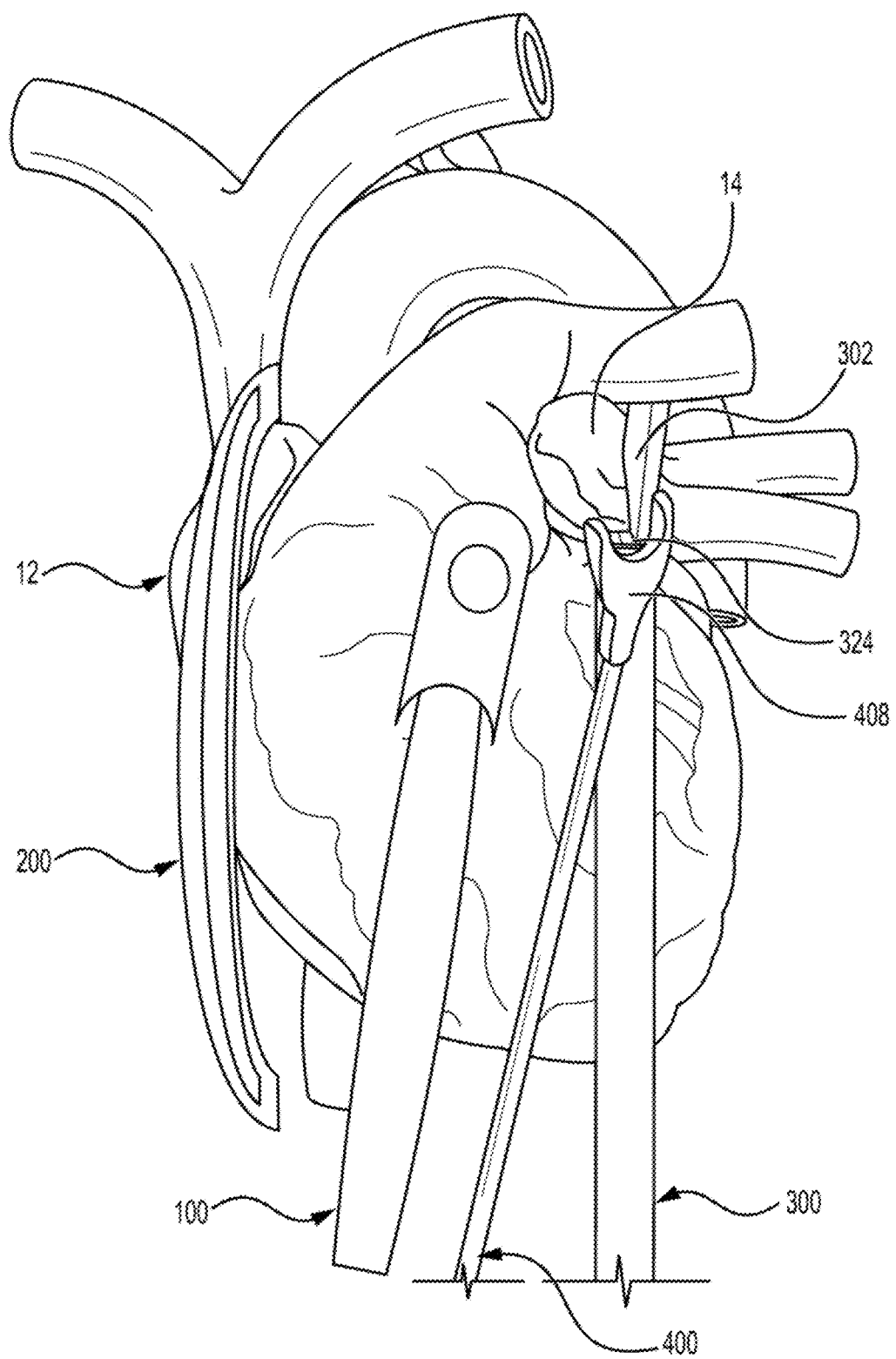

Referring to FIG. 32, the occlusion clip 302 may be opened and/or the clip applier 300 may be positioned to place the occlusion clip 302 at the desired site on the LAA 14, such as by pushing and/or torqueing the clip applier 300 and/or pulling on the introducer 200. If the clip applier 300 includes one or more articulation joints, the end effector 310 may be articulated to facilitate positioning the occlusion clip 302. The positioner 400 may be advanced to proximate the LAA 14 and/or may be used to facilitate locating and/or orienting the occlusion clip 302 as desired. For example, the head 408 of the positioner 400 may be used to push the heel portion 324 of the occlusion clip 302 towards the base of the LAA 14. The occlusion clip 302 may be closed. The position of the occlusion clip 302 on the LAA 14 may be verified visually using the visualization tool 100 and/or using other imaging techniques, such as transesophageal echocardiography. The occlusion clip 302 may be deployed (e.g., released from the clip applier 300). If the clip applier 300 includes a releasably attached distal tip portion 354, the distal tip portion 354 may be released from the jaw member 352, which occur by operation of an actuator on the handle 306 of the clip applier 300 that is used to the deploy the occlusion clip 302.

Figure 33:
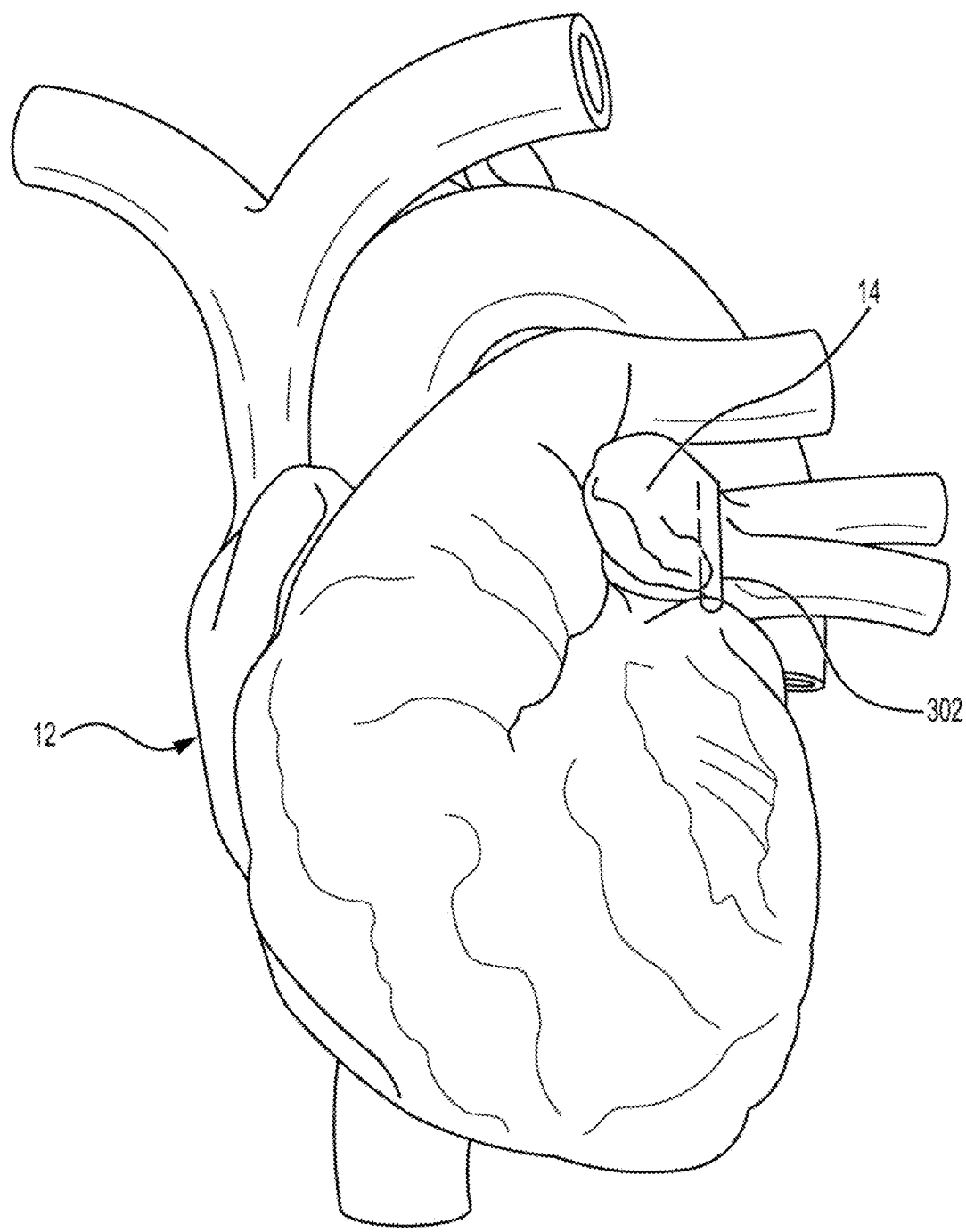

Referring to FIG. 33, the introducer 200, the clip applier 300, the positioner 400, and/or the visualization tool 100 may be withdrawn. The occlusion clip 302 may remain on the LAA 14 and/or may be operative to exclude the LAA 14. The incision(s) may be closed and/or one or more drains may be placed.

Example embodiments according to at least some aspects of the present disclosure may be configured for use with any desired occlusion devices, including those disclosed in the patent references incorporated by reference herein. Example embodiments according to at least some aspects of the present disclosure may be utilized in connection with surgical procedures, such as occlusion procedures, involving any occludable structure in a patient's body.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope as defined by the following claims. Likewise, it is to be understood that it is not necessary to meet any or all of the identified advantages or objects disclosed herein in order to fall within the scope of the claims, since inherent and/or unforeseen advantages may exist even though they may not have been explicitly discussed herein.

What is claimed is:

1. A system for applying a permanent occlusion clip to an anatomical structure, the system comprising:
   a visualization tool configured to allow visualization of an anatomical structure using a scope, the visualization tool independently repositionable with respect to the clip applier;
   a clip applier configured to apply a permanent occlusion clip on the anatomical structure; and
   an introducer independently repositionable with respect to the clip applier when uncoupled thereto so that not to aid in repositioning the clip applier proximate the anatomical structure;
   wherein the introducer comprises an elongated, generally flexible distal section and an elongated, generally flexible proximal section; and
   wherein a proximal end portion of the distal section is configured to releasably couple to a distal end portion of the proximal section.

2. The system of claim 1, further comprising a positioner configured to apply at least one of a linear force and a torsional force to at least one of the clip applier and the occlusion clip.

3. The system of claim 1, wherein the visualization tool comprises
   an elongated, generally rigid shaft;
   a handle disposed at a proximal end portion of the shaft; and
   a scope hood disposed at a distal end portion of the shaft.

4. The system of claim 3,
   wherein the visualization tool comprises a first channel extending longitudinally through the shaft; and
   wherein the first channel is configured to receive at least one of a guidewire, a guide sheath, and the introducer therethrough.

5. The system of claim 4,
   wherein the scope comprises an endoscope; and
   wherein the endoscope extends through a second channel extending longitudinally through the shaft.

6. The system of claim 1, wherein the visualization tool comprises
   an elongated, substantially malleable shaft;
   a handle disposed at a proximal end portion of the shaft; and
   a scope hood disposed at a distal end portion of the shaft.

7. The system of claim 1,
   wherein the proximal end portion of the distal section comprises a first connector and the distal end portion of the proximal section comprises a second connector; and
   wherein the first connector and the second connector are releasably connectable.

8. The system of claim 7,
   wherein the clip applier comprises a distal tip portion, the distal tip portion comprising a third connector; and
   wherein the second connector is connectable to the third connector to connect the introducer to the clip applier.

9. The system of claim 8, wherein, when the second connector is connected to the third connector, the second connector and the third connector are not readily detachable by pulling apart the second connector and the third connector.

10. The system of claim 9,
    wherein the clip applier comprises a first jaw and a second jaw, at least one of the first jaw and the second jaw being articulable to open and close the occlusion clip; and
    wherein the first jaw comprises a jaw member and the distal tip portion, the distal tip portion being releasably attached to the jaw member.

11. A system for applying a permanent occlusion clip to an anatomical structure, the system comprising:
    a visualization tool configured to allow visualization of an anatomical structure using a scope;
    a clip applier configured to apply a permanent occlusion clip on the anatomical structure; and
    an introducer independently repositionable with respect to the clip applier when uncoupled thereto, the introducer configured to releasably couple intraoperatively to the clip applier for aiding in repositioning the clip applier proximate the anatomical structure;
    wherein:
        at least one of the clip applier and the introducer includes a magnet for releasably coupling the introducer and the clip applier;
        the clip applier includes an end effector configured to deliver and apply the permanent occlusion clip on the anatomical structure;
        the end effector comprises a distal tip portion that is connectable to an end portion of the introducer;
        the end portion of the introducer comprises a first connector;
        the distal tip portion of the end effector comprises a second connector; and
        the first connector and the second connector are connectable via the magnet.

12. The clip applier of claim 11, wherein:
    one of the first connector and the second connector includes a latch;
    the other of the first connector and the second connector includes a flange; and
    when the first connector and the second connector are connected, the latch engages the flange to prevent the first connector and the second connector from separating.

13. The clip applier of claim 11, wherein:
    one of the first connector and the second connector includes a radially extending projection;
    the other of the first connector and the second connector includes a slot; and
    when the first connector and the second connector are connected, the projection is retained in the slot via the magnet.

14. The clip applier of claim 13, wherein:
    the slot comprises a generally longitudinal entry slot, a generally circumferential rotation slot, and a generally longitudinal, dead-end locking slot; and
    when the first connector and the second connector are connected, the projection is retained in the locking slot.

* * * * *